United States Patent [19]

Schaap et al.

[11] Patent Number: 5,652,345
[45] Date of Patent: Jul. 29, 1997

[54] 1,2-DIOXETANE COMPOUND

[75] Inventors: Arthur Paul Schaap; Hashem Akhavan-Tafti, both of Detroit, Mich.

[73] Assignee: Tropix, Inc., Bedford, Mass.

[21] Appl. No.: 186,461

[22] Filed: Jan. 25, 1994

Related U.S. Application Data

[63] Continuation of Ser. No. 289,837, Dec. 27, 1988, Pat. No. 5,616,729, which is a continuation-in-part of Ser. No. 887,139, Jul. 17, 1986.

[51] Int. Cl.$^6$ ........................................... C07H 3/00
[52] U.S. Cl. ........................ 536/4.1; 549/332; 549/510
[58] Field of Search ....................................... 536/4.1

[56] References Cited

U.S. PATENT DOCUMENTS 4,315,998  2/1982  Neckers et al. ..................... 525/332

FOREIGN PATENT DOCUMENTS 1044639  12/1979  Canada .

OTHER PUBLICATIONS

F. McCapra, Chem. Commun., 155 (1968).
O. Shimomura et al., Photochem. Photobiol., 30, 89 (1979).
Kopecky, K.R., et al., Can. J. Chem., 47, 709 (1969).
Bartlett, P.D., et al., J. Amer. Chem. Soc., 92, 3223 (1970).
Mazur et al., J. Amer. Chem. Soc., 92, 3225 (1970).
A.P. Schaap et al., J. Amer. Chem. Soc., 99, 1270 (1977).
K.A. Zaklika et al., J. Amer. Chem. Soc., 100, 318 (1978).
K.A. Zaklika et al., J. Amer. Chem. Soc., 100, 4916 (1978).
K.A. Zaklika et al., Photochem. Photobiol., 30, 35 (1979).
A.P. Schaap et al., Organic Photochemical Synthesis, II, 49 (1976).
A.P. Schaap et al., J. Amer. Chem. Soc., 97, 3741 (1975).
A.P. Schaap et al., J. Amer. Chem. Soc., 101 4016 (1979).
J.H. Wieringa et al., Tetrahedron Lett., 169 (1972).
N.J. Turro et al., J. Amer. Chem. Soc., 97, 7110 (1975).
W. Adam et al., Z. Naturforsch., 39b, 679 (1984).
H. Wynberg et al., Bioluminescence & Chemiluminescence, Deluca & McElroy (Eds.) Acad. Press, New York, p. 687, (1981).
J.C. Hummelen et al., Methods in Enzymology, 133B, 531 (1986).
F. McCapra et al., J. Chem. Soc., Chem. Commun., 944 (1977).
W. Adam et al., Chem. Ber., 116,839 (1983).
G. Geller et al., Tetrahedron Lett., 673 (1983).
P. Lechtken, Chem. Ber., 109, 2862 (1976).
P.D. Bartlett et al., J. Amer. Chem. Soc., 96, 627 (1974).
A.P. Schaap et al., J. Amer. Chem. Soc., 104, 3504 (1982).
A.P. Schaap et al., Tetrahedron Lett., 2943 (1982).
R.S. Handley et al., Tetrahedron Lett., 3183 (1985).
A.P. Schaap et al., Tetrahedron Lett., 935 (1987).
A.P. Schaap et al., Tetrahedron Lett., 1155 (1987).
A.P. Schaap et al., Tetrahedron Lett., 1159 (1987).
J.E. McMury et al., J. Amer. Chem. So., 105, 1660 (1983).
T. Wilson, Int. Rev. Sci.: Chem. Ser. Two, 9, 265 (1976).
T. Wilson et al., J. Amer. Chem. Soc., 95, 4765 (1973).
P.D. Bartlett et al., J. Amer. Chem. Soc., 96, 5557 (1974).
T. Wilson et al., J. Amer. Chem. Soc., 93, 4126 (1971).
W. Adam In Chemical & Biological Generation of Excited States, W. Adam & G. Cilento, eds. Ch.4, Acad. Press, New York, 1982.
M.A. Ribi et al., Tetrahedron, 28, 481 (1972).
G. Thorpe et al., Pure & Appl. Chem., 59, 651 (1987).
J. Lee et al., Photochem. Photobiol., 15, 227 (1972).
P.R. Michael et al., Anal. Chem., 48, 1188 (1976).

*Primary Examiner*—Amelia A. Owens
*Attorney, Agent, or Firm*—Oblon, Spivak, McClelland, Maier & Neustadt, P.C.

[57] ABSTRACT

4-(3-beta-D-galactopyranosylphenyl)-4-methoxyspiro[1,2-dioxetane-3,2'-adamantane] which is useful in various chemiluminescent assays.

1 Claim, 3 Drawing Sheets

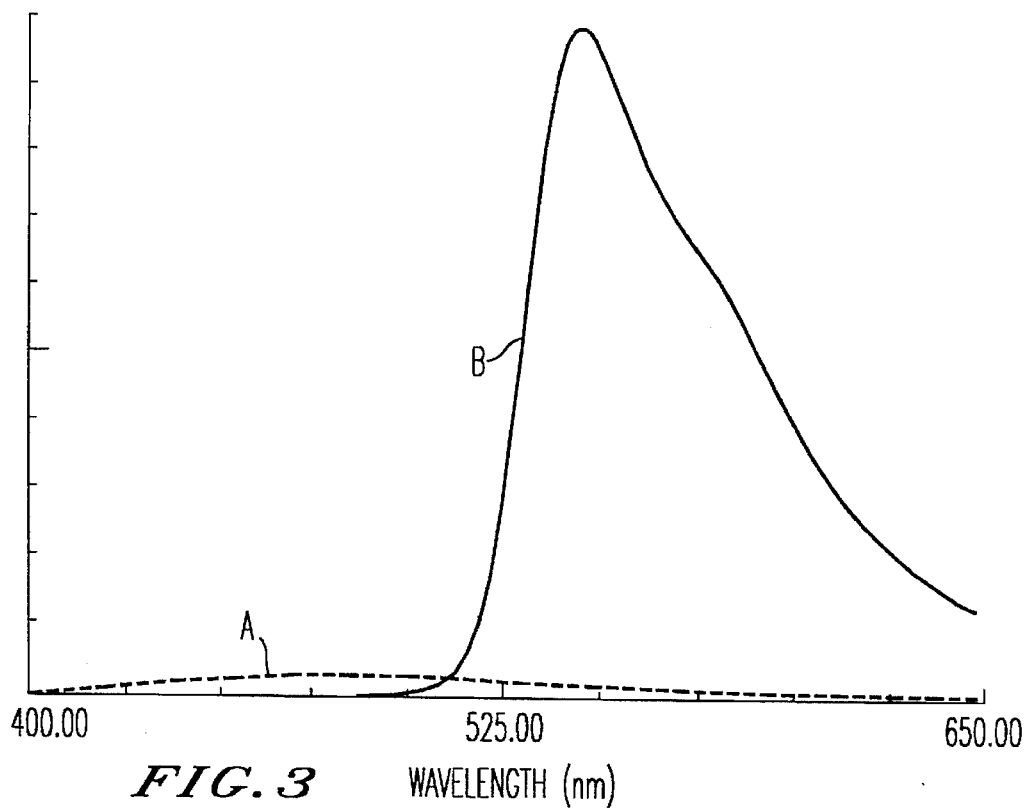
FIG. 3 WAVELENGTH (nm)
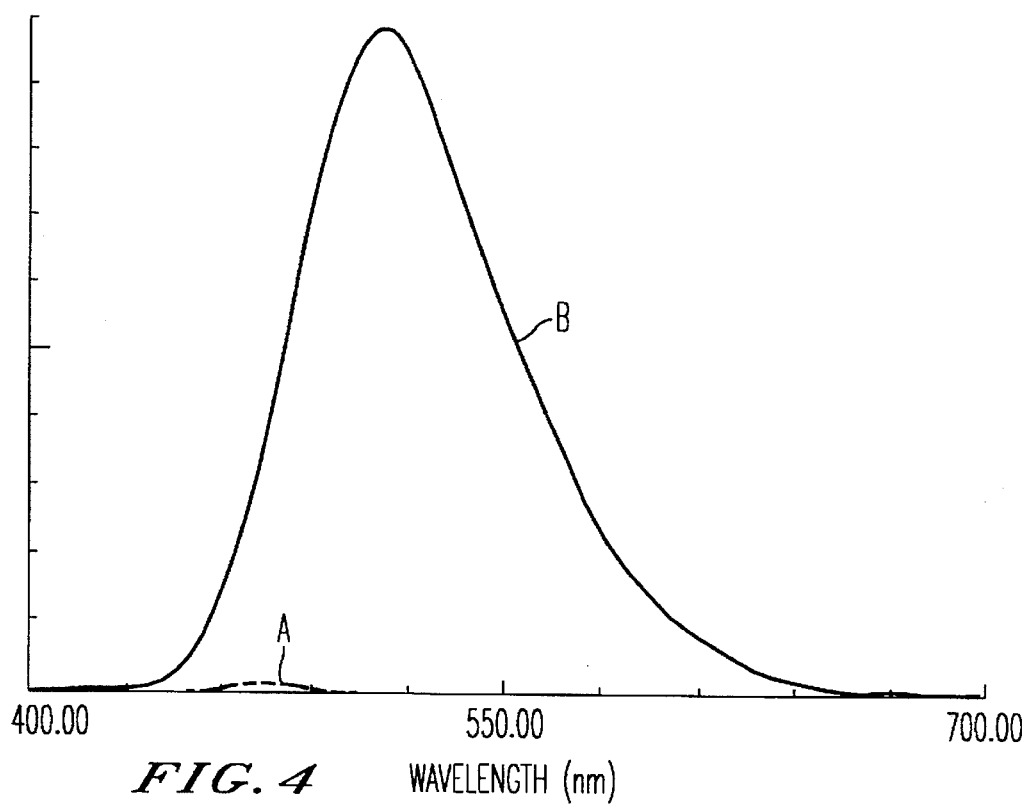
FIG. 4 WAVELENGTH (nm)

1,2-DIOXETANE COMPOUND

CROSS-REFERENCE TO RELATED APPLICATION

This is a continuation of application Ser. No. 07/289,837, filed on Dec. 27, 1988 now U.S. Pat. No. 5,616,729 which is a continuation-in-part of U.S. application Ser. No. 887,139, filed Jul. 17, 1986 now pending.

BACKGROUND OF THE INVENTION

(1) Statement of the Invention

The present invention relates to thermally stable dioxetanes which can be triggered by chemical reagents or enzymes to generate chemiluminescence in organic solvents or in aqueous solution. A method for significantly enhancing the chemiluminescence efficiency has been discovered which involves intramolecular energy transfer to a fluorescent group which is bonded or "tethered" to the dioxetane molecule. These compounds can be used in various chemiluminescent assays including enzyme-linked immunoassays and enzyme-linked DNA probes as well as direct, chemically triggerable labels for biomolecules.

(2) Prior Art

1. Mechanisms of Luminescence.

Exothermic chemical reactions release energy during the course of the reaction. In virtually all cases, this energy is in the form of vibrational excitation or heat. However, a few chemical processes generate light or chemiluminescence instead of heat. The mechanism for light production involves thermal or catalyzed decomposition of a high energy material (frequently an organic peroxide such as a 1,2-dioxetane) to produce the reaction product in a triplet or singlet electronic excited states. Fluorescence of the singlet species results in what has been termed direct chemiluminescence. The chemiluminescence quantum yield is the product of the quantum yields for singlet chemiexcitation and fluorescence. These quantities are often expressed as efficiencies where efficient $(\%) = \phi \times 100$. Energy transfer from the triplet or singlet product to a fluorescent acceptor can be utilized to give indirect chemiluminescence. The quantum yield for indirect chemiluminescence is the product of the quantum yields for singlet or triplet chemiexcitation, energy transfer, and fluorescence of the energy acceptor.

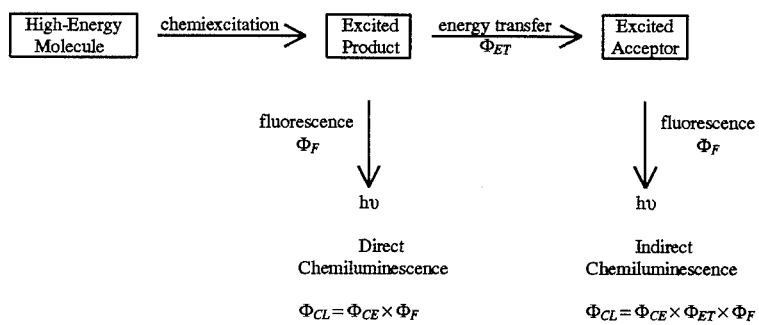

2. Dioxetane Intermediates in Bioluminescence.

In 1968 McCapra proposed that 1,2-dioxetanes might be the key high-energy intermediates in various bioluminescent reactions including the firefly system. (F. McCapra, *Chem. Commun.*, 155 (1968)). Although this species is apparently quite unstable and has not been isolated or observed spectroscopically, unambiguous evidence for its intermediacy in the reaction has been provided by oxygen-18 labeling experiments. (O. Shimomura and F. H. Johnson, *Photochem. Photobiol.*, 30, 89 (1979)).

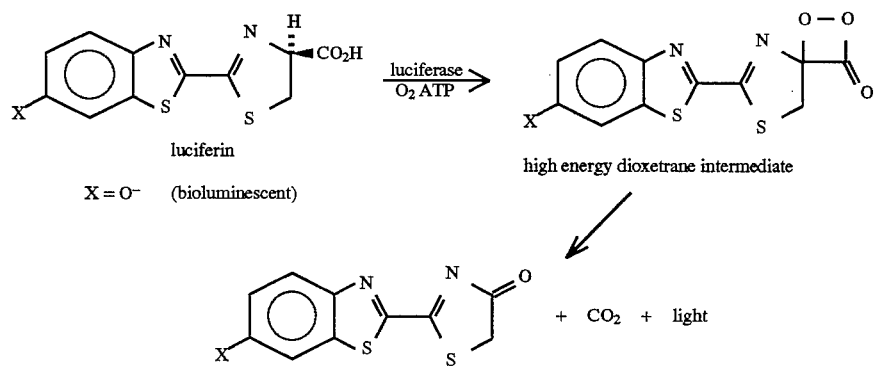

3. First Synthesis of Authentic 1,2-Dioxetanes.

In 1969 Kopecky and Mumford reported the first synthesis of a dioxetane (3,3,4-trimethyl-1,2-dioxetane) by the base-catalyzed cyclization of a beta-bromohydroperoxide. (K. R. Kopecky and C. Mumford, *Can. J. Chem.*, 47, 709 (1969)). As predicted by McCapra, this dioxetane did, in fact, produce chemiluminescence upon heating to 50° C. with decomposition to acetone and acetaldehyde. However, this peroxide is relatively unstable and cannot be stored at room temperature (25° C.) without rapid decomposition. In addition, the chemiluminescence efficiency is very low (less than 0.1%).

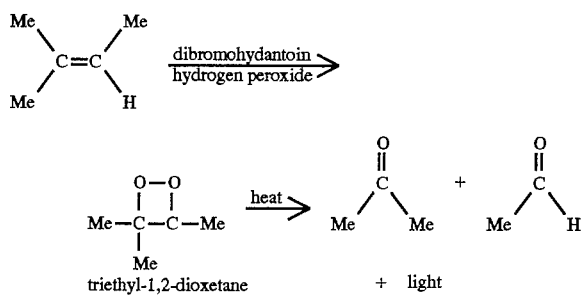

triethyl-1,2-dioxetane + light

Bartlett and Schaap and Mazur and Foote independently developed an alternative and more convenient synthetic route to 1,2-dioxetanes. Photooxygenation of properly-substituted alkenes in the presence of molecular oxygen and a photosensitizing dye produces dioxetanes in high yields. (P. D. Bartlett and A. P. Schaap, J. Amer. Chem. Soc., 92, 3223 (1970) and S. Mazur and C. S. Foote, J. Amer. Chem. Soc., 92, 3225 (1970)). The mechanism of this reaction involves the photochemical generation of a metastable species known as singlet oxygen which undergoes 2+2 cycloaddition with the alkene to yield the dioxetane. Research has shown that a variety of dioxetanes can be prepared using this reaction (A. P. Schaap, P. A. Burns, and K. A. Zaklika, J. Amer. Chem. Soc., 99, 1270 (1977); K. A. Zaklika, P. A. Burns, and A. P. Schaap, J. Amer. Chem. Soc., 100, 318 (1978); K. A. Zaklika, A. L. Thayer, and A. P. Schaap, J. Amer. Chem. Soc., 100, 4916 (1978); K. A. Zaklika, T. Kissel, A. L. Thayer, P. A. Burns, and A. P. Schaap, Photochem. Photobiol., 30, 35 (1979); and A. P. Schaap, A. L. Thayer, and K. Kees, Organic Photochemical Synthesis, II, 49 (1976)). During the course of this research, a polymer-bound sensitizer for photooxygenations was developed (A. P. Schaap, A. L. Thayer, E. C. Blossey, and D. C. Neckers, J. Amer. Chem. Soc., 97, 3741 (1975); and A. P. Schaap, A. L. Thayer, K. A. Zaklika, and P. C. Valenti, J. Amer. Chem. Soc., 101, 4016 (1979)). This new type of sensitizer has been patented and sold under the tradename SENSITOX™ (U.S. Pat. No. 4,315,998 (Feb. 16, 1982); Canadian Patent No. 1,044,639 (Dec. 19, 1979)). Over fifty references have appeared in the literature reporting the use of this product.

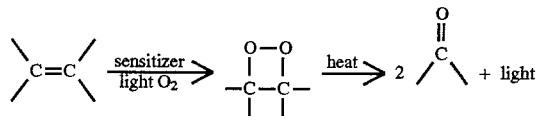

4. Preparation of Stable Dioxetanes Derived from Sterically Hindered Alkenes.

Wynberg discovered that photooxygenation of sterically hindered alkenes such as adamantylideneadamantane affords a very stable dioxetane (J. H. Wieringa, J. Strating, H. Wynberg, and W. Adam, Tetrahedron Lett., 169 (1972)). A collaborative study by Turro and Schaap showed that this dioxetane exhibits an activation energy for decomposition of 37 kcal/mol and a half-life at room temperature (25° C.) of over 20 years (N. J. Turro, G. Schuster, H. C. Steinmetzer, G. R. Faler, and A. P. Schaap, J. Amer. Chem. Soc., 97, 7110 (1975)). In fact, this is the most stable dioxetane yet reported in the literature. Adam and Wynberg have recently suggested that functionalized adamantylideneadamantane 1,2-dioxetanes may be useful for biomedical applications (W. Adam, C. Babatsikos, and G. Cilento, Z. Naturforsch., 39b, 679 (1984); H. Wynberg, E. W. Meijer, and J. C. Hummelen, In Bioluminescence and Chemiluminescence, M. A. DeLuca and W. D. McElroy (Eds.) Academic Press, New York, p. 687, 1981; and J. C. Hummelen, T. M. Luider, and H. Wynberg, Methods in Enzymology, 133B, 531 (1986)). However, use of this extraordinarily stable peroxide for chemiluminescent labels requires detection temperatures of 150° to 250° C. Clearly, these conditions are unsuitable for the evaluation of biological analytes in aqueous media. McCapra, Adam, and Foote have shown that incorporation of a spirofused cyclic or polycyclic alkyl group with a dioxetane can help to stabilize dioxetanes that are relatively unstable in the absence of this sterically bulky group (F. McCapra, I. Beheshti, A. Burford, R. A. Hann, and K. A. Zaklika, J. Chem. Soc., Chem. Commun., 944 (1977); W. Adam, L. A. A. Encarnacion, and K. Zinner, Chem. Ber., 116, 839 (1983); G. G. Geller, C. S. Foote, and D. B. Pechman, Tetrahedron Lett., 673 (1983); P. Lechtken, Chem. Ber., 109, 2862 (1976); and P. D. Bartett and M. S. Ho, J. Amer. Chem. Soc., 96, 627 (1974))

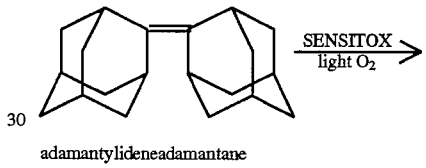

adamantylideneadamantane

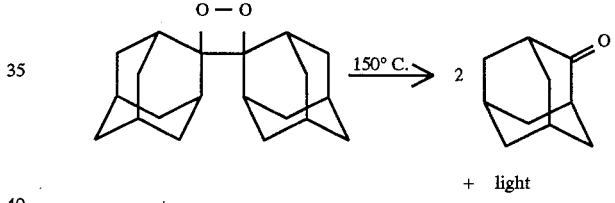

+ light

5. Effects of Substituents on Dioxetane Chemiluminescence.

The stability and the chemiluminescence efficiency of dioxetanes can be altered by the attachment of specific substituents to the peroxide ring (K. A. Zaklika, T. Kissel, A. L. Thayer, P. A. Burns, and A. P. Schaap, Photochem. Photobiol., 30, 35 (1979); A. P. Schaap and S. Gagnon, J. Amer. Chem. Soc., 104, 3504 (1982); A. P. Schaap, S. Gagnon, and K. A. Zaklika, Tetrahedron Lett., 2943 (1982); and R. S. Handley, A. J. Stern, and A. P. Schaap, Tetrahedron Lett., 3183 (1985)). The results with the bicyclic system shown below illustrate the profound effect of various functional groups on the properties of dioxetanes. The hydroxy-substituted dioxetane (X=OH) derived from the 2,3-diaryl-1,4-dioxene exhibits a half-life for decomposition at room temperature (25° C.) of 57 hours and produces very low levels of luminescence upon heating at elevated temperatures. In contrast, however, reaction of this dioxetane with a base at −30° C. affords a flash of blue light visible in a darkened room. Kinetic studies have shown that the deprotonated dioxetane (X=O⁻) decomposes $5.7 \times 10^6$ times faster than the protonated form (X=OH) at 25° C.

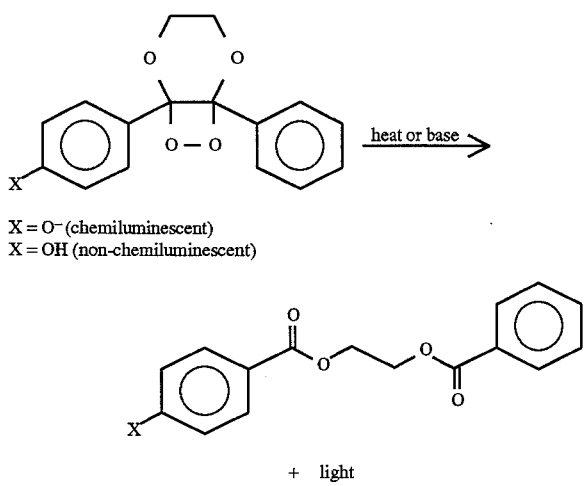

X = O⁻ (chemiluminescent)
X = OH (non-chemiluminescent)

+ light

The differences in the properties of these two dioxetanes arise because of two competing mechanisms for decomposition ((K. A. Zaklika, T. Kisse, A. L. Thayer, P. A. Burns, and A. P. Schaap, *Photochem. Photobiol.*, 30, 35 (1979); A. P. Schaap and S. Gagnon, *J. Amer. Chem. Soc.*, 104, 3504 (1982); A. P. Schaap, S. Gagnon, and K. A. Zaklika, *Tetrahedron Lett.*, 2943 (1982); and R. S. Handley, A. J. Stern, and A. P. Schaap, *Tetrahedron Lett.*, 3183 1985)). Most dioxetanes cleave by a process that involves homolysis of the O—O bond and formation of a biradical. An alternative mechanism is available to dioxetanes bearing substituents such as O⁻ with low oxidation potentials. The cleavage is initiated by intramolecular electron transfer from the substituent to the antibonding orbital of the peroxide bond.

6. Chemical Triggering of Stabilized 1,2-Dioxetanes.

We have recently discovered that thermally stable dioxetanes can be triggered by chemical and enzymatic processes to generate chemiluminescence on demand (A. P. Schaap, patent application Ser. No. 887,139, filed Jul. 15, 1986; A. P. Schaap, R. S. Handley, and B. P. Giri, *Tetrahedron Lett.*, 935 (1987); A. P. Schaap, T. S. Chen, R. S. Handley, R. DeSilva, and B. P. Giri, *Tetrahedron Lett.*, 1155 (1987); and A. P. Schaap, M. D. Sandison, and R. S. Handley, *Tetrahedron Lett.*, 1159 (1987)). To do this, we have developed new synthetic procedures to produce dioxetanes with several key features: (1) the stabilizing influence of spiro-fused adamantyl groups has been utilized to provide dioxetanes that have "shelf lives" of years at ambient temperature and (2) new methods for triggering the chemiluminescent decomposition of the stabilized dioxetanes have been provided.

The required alkenes have been prepared by reaction of 2-adamantanone with aromatic esters or ketones using titanium trichloride/LAH in THF (A. P. Schaap, patent application Ser. No. 887,139). This is the first report of the intermolecular condensation of ketones and esters to form vinyl ethers using the McMurry procedure. Although McMurry had earlier investigated the intramolecular reaction of ketone and ester functional groups, cyclic ketones and not vinyl ethers were prepared by this method (J. E. McMury and D. D. Miller, *J. Amer. Chem. Soc.*, 105, 1660 (1983)).

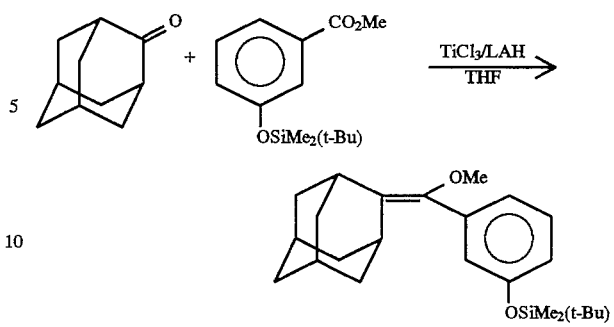

Photooxygenation of these vinyl ethers affords dioxetanes that are easily handled compounds with the desired thermal stability. For example, the dioxetane shown below exhibits an activation energy of 28.4 kcal/mol and a half-life at 25° C. of 3.8 years. Samples of this dioxetane in o-xylene have remained on the laboratory bench for several months with no detectable decomposition.

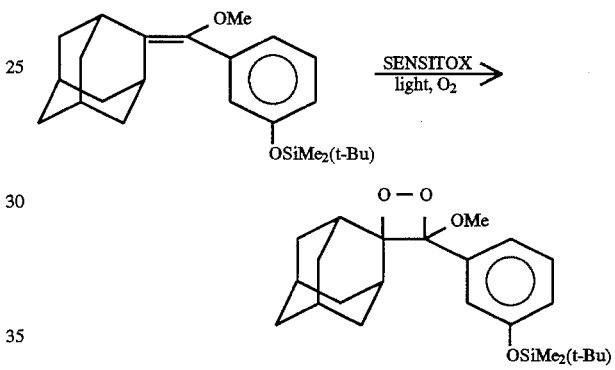

However, the chemiluminescent decomposition of this dioxetane can be conveniently triggered at room temperature by removal of the silyl-protecting with fluoride ion to generate the unstable, aryloxide form which cleaves to yield intense blue light. The half-life of the aryloxide-substituted dioxetane is 5 seconds at 25° C. The spectrum of the chemiluminescence in DMSO exhibited a maximum at 470 nm which is identical to the fluorescence of the anion of the ester cleavage product (methyl 3-hydroxybenzoate) and the fluorescence of the spent dioxetane solution under these conditions. No chemiluminescence derived from adamantanone fluorescence appears to be produced. Chemiluminescence quantum yields for the fluoride-triggered decomposition measured relative to the luminol standard was determined to be 0.25 (or a chemiluminescence efficiency of 25%). Correction for the fluorescence quantum yield of the ester under these conditions ($\phi_F$=0.44) gave an efficiency for the formation of the singlet excited ester of 57%, the highest singlet chemiexcitation efficiency yet reported for a dioxetane prepared in the laboratory.

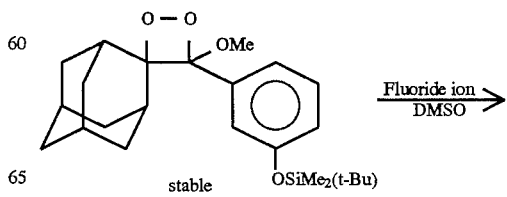

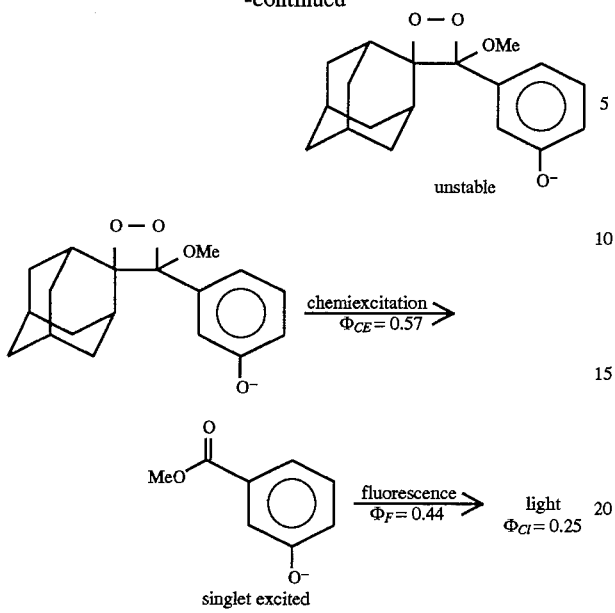

7. Enzymatic Triggering of 1,2-Dioxetanes.

Biological assays such as immunoassays and DNA probes involving enzymes utilize a wide variety of substrates which either form a color (chromogenic) or become fluorescent (fluorogenic) upon reaction with the enzyme. As part of our investigation of triggering methods, we developed the first dioxetanes which can function as chemiluminescent enzyme substrates (A. P. Schaap, patent application Ser. No. 887, 139; A. P. Schaap, R. S. Handley, and B. P. Giri, *Tetrahedron Lett.*, 935 (1987); A. P. Schaap, T. S. Chen, R. S. Handley, R. DeSilva, and B. P. Giri, *Tetrahedron Lett.*, 1155 (1987); and A. P. Schaap, M. D. Sandison, and R. S. Handley, *Tetrahedron Lett.*, 1159 (1987)). Use of these peroxides in biological systems requires dioxetanes which are thermally stable at the temperature of the enzymatic reaction and do not undergo rapid spontaneous decomposition in the aqueous buffers. The spiro-fused adamantyl dioxetanes described in the previous section meet these requirements. We have, therefore, prepared dioxetanes bearing functional groups which can be enzymatically modified to generate the aryloxide form. Decomposition of this unstable intermediate provides the luminescence. Dioxetanes have been synthesized which can be triggered by various enzymes including aryl esterase, acetylcholinesterase, and alkaline phosphatase. The phosphatase example is particularly significant because this enzyme is used extensively in enzyme-linked immunoassays.

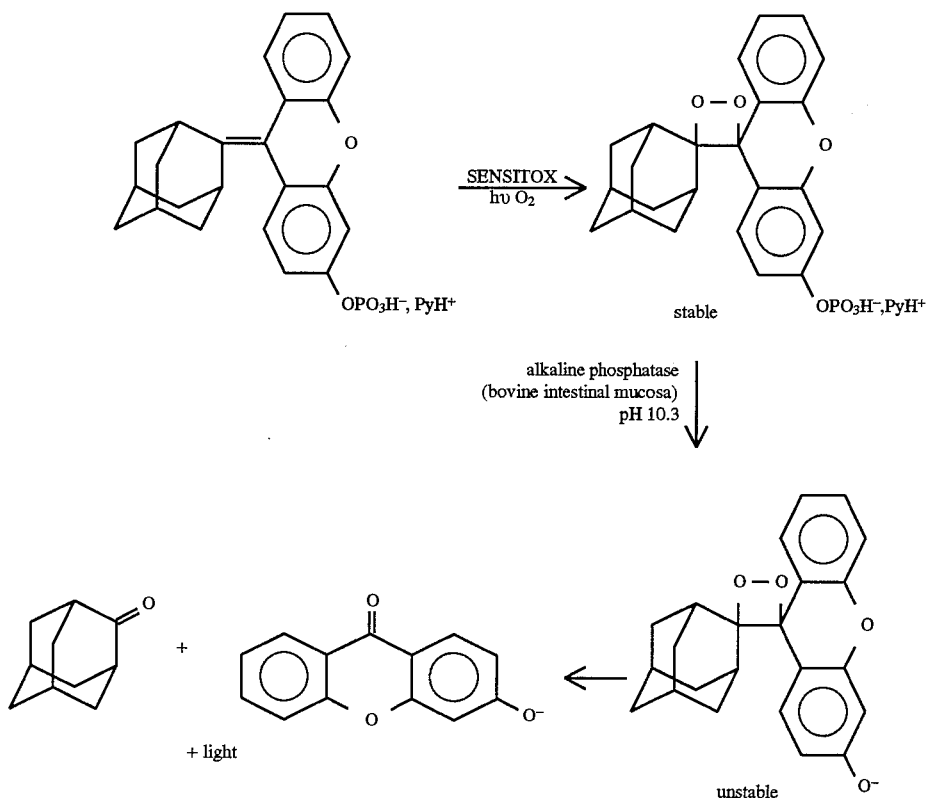

For example, enzymatic triggering by alkaline phosphatase was observed with the phosphate-substituted dioxetane derived from 3-hydroxy-9H-xanthen-9-one and 2-adamantanone. The dioxetane is thermally stable with an activation energy of 30.7 kcal/mol and a half-life at 25° C. of 12 years. The dioxetane is not only stable in organic solvents but also shows very slow spontaneous decomposition in aqueous buffers.

Triggering experiments were conducted using alkaline phosphatase from bovine intestinal mucosa [suspension of 5.3 mg of protein (1100 units/mg protein) per mL in 3.2 $\underline{M}$ $(NH_4)_2SO_4$] and the phosphate-protected dioxetane at pH 10.3 in 0.75$\underline{M}$ 2-amino-2-methyl-1-propanol buffer. A 50 μL aliquot (0.013 μmol) of a phosphate-dioxetane stock solution was added to 3 mL of the buffer at 37° C. to give a final dioxetane concentration of $4.2 \times 10^{-6}\underline{M}$. Injection of 1 μL (final concentration of protein=1.8 μg/mL) of alkaline phosphatase to the solution resulted in burst of chemiluminescence that decayed over a period of 3 minutes. Over this period of time, the background luminescence from slow non-enzymatic hydrolysis of the dioxetane in the buffer was only 0.2% of that produced by the enzymatic process. The total light emission was found to be linearly dependent on the dioxetane concentration. The rate of decay of the emission is a function of enzyme concentration while the total light emission is independent of the enzyme concentration. The chemiluminescence spectrum for the phosphatase-catalyzed decomposition was obtained at room temperature in the buffer solution. A comparison of this chemiluminescence spectrum with the fluorescence spectrum of the spent reaction mixture and the fluorescence spectrum of the hydroxyxanthanone cleavage product in the buffer indicates that the emission is initiated by the enzymatic cleavage of the phosphate group in dioxetane to yield the unstable aryloxide dioxetane which generates the singlet excited anion of hydroxyxanthanone.

Literature Examples (a) Chemical Triggering of Dioxetanes:

The first example in the literature is described above (A. P. Schaap and S. Gagnon, *J. Amer. Chem. Soc.*, 104, 3504 (1982)). However, the hydroxy-substituted dioxetane and any other examples of the dioxetanes derived from the diaryl-1,4-dioxenes are far too unstable to be of use in any application. They have half-lives at 25° C. of only a few hours. Neither the dioxetane nor the precursor alkene would survive the conditions necessary to prepare derivatives. Further, these non-stabilized dioxetanes are destroyed by small quantities of amines (T. Wilson, *Int. Rev. Sci.: Chem., Ser. Two*, 9, 265 (1976)) and metal ions (T. Wilson, M. E. Landis, A. L. Baumstark, and P. D. Bartlett, *J. Amer. Chem. Soc.*, 95, 4765 (1973); P. D. Bartlett, A. L. Baumstark, and M. E. Landis, *J. Amer. Chem. Soc.*, 96, 5557 (1974) and could not be used in the aqueous buffers required for enzymatic triggering.

The only examples of the chemical triggering of stabilized dioxetanes are reported in the prior patent application (A. P. Schaap, patent application Ser. No. 887,139) and a paper (A. P. Schaap, T. S. Chen, R. S. Handley, R. DeSilva, and B. P. Giri, *Tetrahedron Lett.*, 1155 (1987)). These dioxetanes exhibit thermal half-lives of years but can be triggered to produce efficient chemiluminescence on demand.

(b) Enzymatic triggering of Dioxetanes.

Examples of enzymatic triggering of dioxetanes are described in the prior patent applications (A. P. Schaap, patent application Ser. No. 887,139) and papers (A. P. Schaap, R. S. Handley, and B. P. Giri, *Tetrahedron Lett.*, 935 (1987) and A. P. Schaap, M. D. Sandison, and R. S. Handley, *Tetrahedron Lett.*, 1159 (1987)).

(c) Energy-Transfer Chemiluminescence Involving Dioxetanes in Homogeneous Solution.

The first example of energy-transfer chemiluminescence involving dioxetanes was described by Wilson and Schaap (T. Wilson and A. P. Schaap, *J. Amer. Chem. Soc.*, 93, 4126 (1971)). Thermal decomposition of a very unstable dioxetane (cis-diethoxydioxetane) gave both singlet and triplet excited ethyl formate. Addition of 9,10-diphenylanthracene and 9,10-dibromoanthracene resulted in enhanced chemiluminescence through singlet-single and triplet-singlet energy-transfer processes, respectively. These techniques have subsequently been used by many other investigators to determine yields of chemiexcited products generated by the thermolysis of various dioxetanes (For a review, see W. Adam, In *Chemical and Biological Generation of Excited States*, W. Adam and G. Cilento, Eds. Ch. 4, Academic Press, New York, 1982). A. Paul Schaap application Ser. No. 224,681, filed Jul. 27, 1987 shows the use of fluorescers with triggerable dioxetanes.

Energy transfer in homogeneous solution, however, requires high concentrations of the energy acceptor because of the short lifetimes of the electronically excited species. These high concentrations can lead to problems of self-quenching and reabsorption. The present invention solves these problems by using a fluorescer which is chemically bound or tethered to the excited product produced by triggering the dioxetane, thereby obviating the need for high concentrations of a fluorescer in bulk solution.

(d) Enhanced Chemiluminescence from a Dioxetane Using Intramolecular Energy Transfer to a Tethered Fluorescer.

No examples appear in the literature of a fluorescent energy acceptor that is chemically bound or tethered to a dioxetane. The only examples of enhanced chemiluminescence using intramolecular energy transfer derived from the work of White on the luminol system (M. A. Ribi, C. C. Wei, and E. H. White, *Tetrahedron*, 28 481 (1972) and references therein). Chemiluminescence is produced by chemical oxidation of phthalic hydrazides to form electronically excited phthalate ions followed by energy transfer to attached fluorescent groups. Dioxetanes are not involved in these processes.

(e) Enhanced Chemiluminescence from the Luminol/peroxidase Reaction.

A method for enhancing the chemiluminescent yield of the luminol/peroxidase reaction by addition of 6-hydroxybenzothiazole derivatives or para-substituted phenols (G. H. G. Thorpe, L. J. Kricka, S. B. Moseley, T. P. Whitehead, *Clin. Chem.*, 31, 1335 (1985); G. H. G. Thorpe and L. J. Kricka, *Methods in Enzymology*, 133, 331 (1986); and L. J. Kricka, G. H. G. Thorpe, and R. A. W. Scott, *Pure & Appl. Chem.*, 59, 651 (1987)). The mechanism for the enhancement is not known but it does not involve intramolecular energy transfer with a chemically attached fluorescer.

OBJECTS

It is therefore an object of the present invention to provide novel dioxetanes which provide intramolecular transfer of energy to a tethered fluorescer molecule. Further, it is an object of the present invention to provide a process for the preparation of the novel dixoetanes. These and other objects will become increasingly apparent by reference to the following description and the drawings.

IN THE DRAWINGS

FIG. 3 is a graph wherein curve A (____) shows the spectrum of direct chemiluminescence from chemical triggering of dioxetane 2b in water with NaOH ($\lambda_{max}$=470 nm; and curve B (---) shows the spectrum of energy-transfer chemiluminescence from chemical triggering of tethered dioxetane 6 in water with NaOH ($\lambda_{max}$=550 nm).

FIG. 4 is a graph wherein curve A (---) shows the spectrum of direct chemiluminescence from enzymatic triggering of dioxetane 2b in 221 buffer (pH 9.2) with aryl esterase ($\lambda_{max}$=470 nm); and curve B (____) shows the spectrum of energy-transfer chemiluminescence from enzymatic triggering of tethered dioxetane 4b in 221 buffer (pH 9.2) with aryl esterase ($\lambda_{max}$=519 nm).

GENERAL DESCRIPTION

Figure 1:
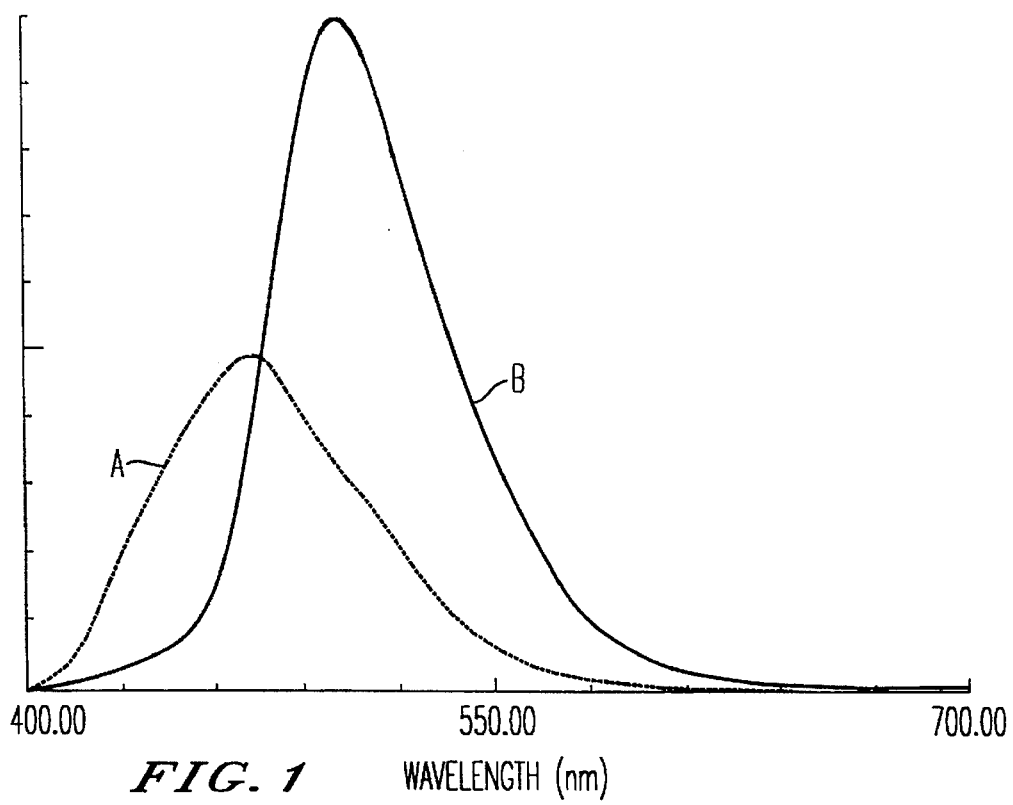
FIG. 1 is a graph wherein curve A (---) shows the spectrum of direct chemiluminescence from chemical triggering of dioxetane 2b in DMSO with fluoride ($\lambda_{max}$=470 nm); and curve B (____) shows the spectrum of energy-transfer chemiluminescence from chemical triggering of tethered dioxetane 4b in DMSO with fluoride ($\lambda_{max}$=508 nm).
Figure 2:
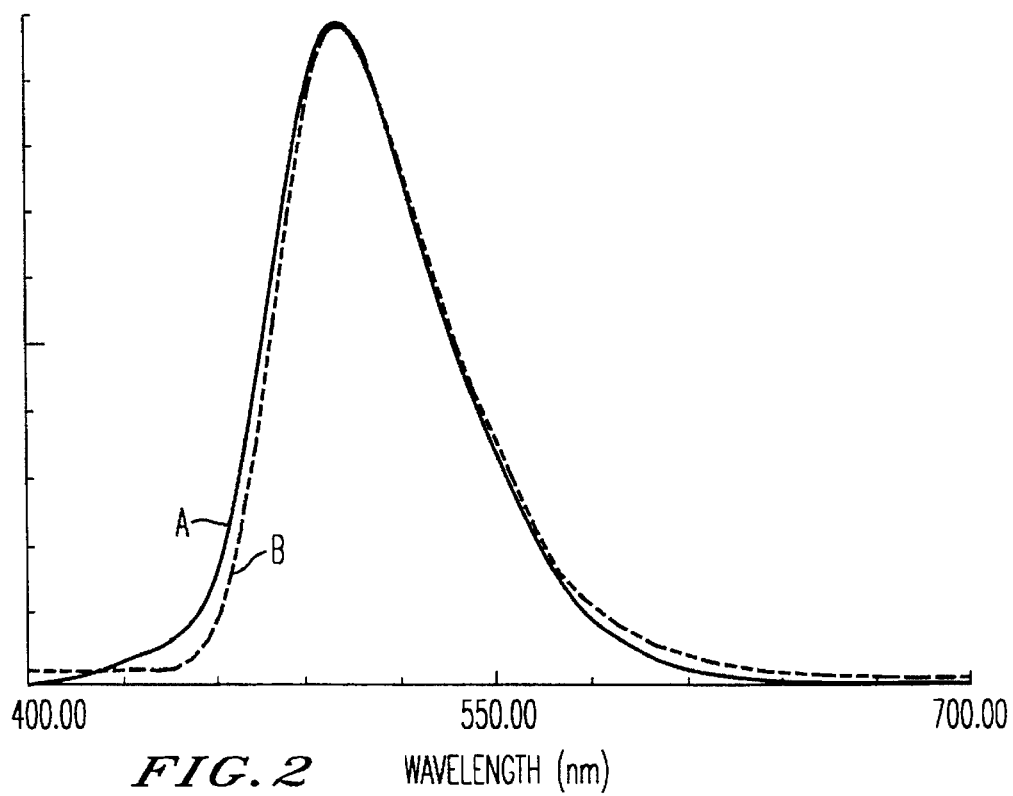
FIG. 2 is a graph wherein curve A (____) shows the chemiluminescence spectrum from chemical triggering of tethered dioxetane 4b in DMSO with fluoride ($\lambda_{max}$=508 nm); and curve B (---) shows the fluorescence spectrum of the cleavage product under the same conditions.

The present invention relates to a dioxetane compound of the formula:

wherein $R_1$, $R_2$ and $R_3$ are carbon containing groups and optionally containing oxygen, nitrogen or sulfur which allow the production of the light, wherein one of $R_1$, $R_2$ and $R_3$ is a tethered fluorescent molecule containing group wherein the fluorescent molecule exhibits fluorescence between approximately 400 and 900 nanometers, wherein $R_1$ and $R_2$ can be joined together, wherein $R_3$ and ArOX can be joined together, wherein X is a leaving group, wherein compound (I) decomposes to form an aryl oxide (II) of the formula

when reacted with an activating agent which removes X, wherein the aryl oxide (II) spontaneously decomposes to form compounds (III) and (IV) of the formulae:

and wherein the fluorescent molecule in the fluorescent molecule containing group is activated to produce light upon the decomposition of the aryl oxide.

Further the present invention relates to a dioxetane compound of the formula:

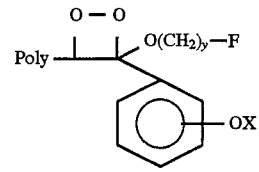

wherein Poly is a spirofused polycyclic alkylene group containing 6 to 30 carbon atoms and optionally oxygen and nitrogen, wherein F is a fluorescent molecule containing group wherein the fluorescent molecule exhibits fluorescence between 400 and 900 nanometers, wherein y is an integer between 1 and 14, and wherein X is a leaving group which when removed by an activating agent produces an oxide intermediate of the dioxetane compound which spontaneously decomposes to form light because of F and carbonyl containing molecules of the formulae

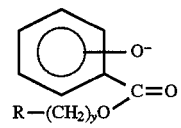

In particular the present invention relates to the compounds wherein OX is an acetoxy group, a hydroxyl group, an o-galactopyranoside group, or a phosphate group.

The fluorescent molecule can be selected from the group consisting of fluorescent dyes, aromatic compounds including benzene derivatives, naphthalene derivatives, anthracene derivatives, pyrenes, biphenyls, acridines, coumarins, xanthenes, phthalocyanines, stilbenes, furans, oxazoles, oxadiazoles, benzothiazoles, fuoresceins, rhodamines, eosins, resorufins, quinolines. The fluorescent molecules are selected to provide fluorescence in the range of about 400 to 900 nanometers.

The preferred process for preparing the compounds generally involves the process for preparing a dioxetane compound (I) of the formula:

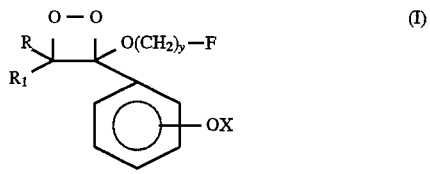

wherein R and $R_1$ are groups which allow the production of light and can be joined together, wherein y is an integer between 1 and 14 and wherein F is a fluorescent molecule group, wherein X is a leaving group, which when removed by an activating agent produces an oxide intermediate of the dioxetane compound which spontaneously decomposes to form light because of F, which comprises: reacting in an organic solvent, a compound (II) of the formula:

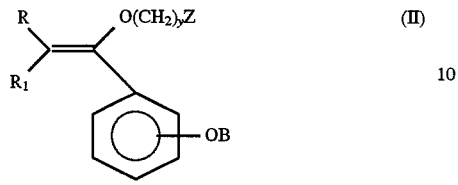

wherein Z is a reactive group, with FA wherein A is reactive with Z to form a compound (III) of the formula:

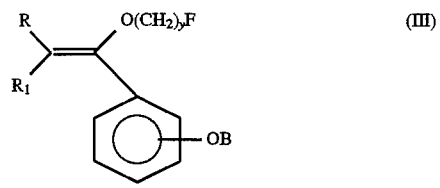

wherein B is a non-photo-oxidatively reactive group selected from the group consisting of X or groups which can be converted to X; and reacting oxygen with compound (III) to form a dioxetane compound of the formula:

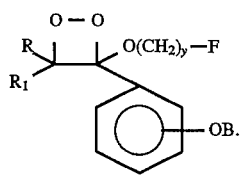

Preferably R and $R_1$ are joined together as a polycyclic group containing 6 to 30 carbon atoms. The OB (or OX) group can be acetoxy or other alkyl or aryl ester groups, phosphate or other inorganic oxyacid salts, alkyl or aryl silyloxy, hydroxyl, oxygen-pyranoside such as beta-galactopyranosyl and the like.

SPECIFIC DESCRIPTION

The following is a schematic of the compounds synthesized:

1,2-Dioxetane Compounds Synthesized

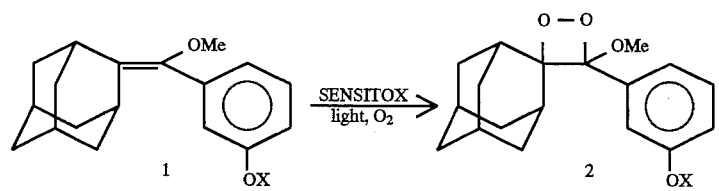

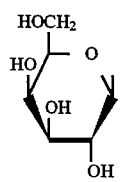

(a) X = H
(b) X = Ac
(c) X = β-D-gactopyranosyl =
(d) X = OPO$_3$Na$_2$

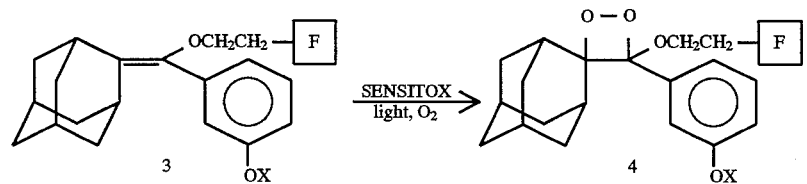

(a) X = H
(b) X = Ac

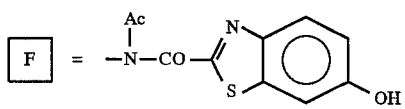

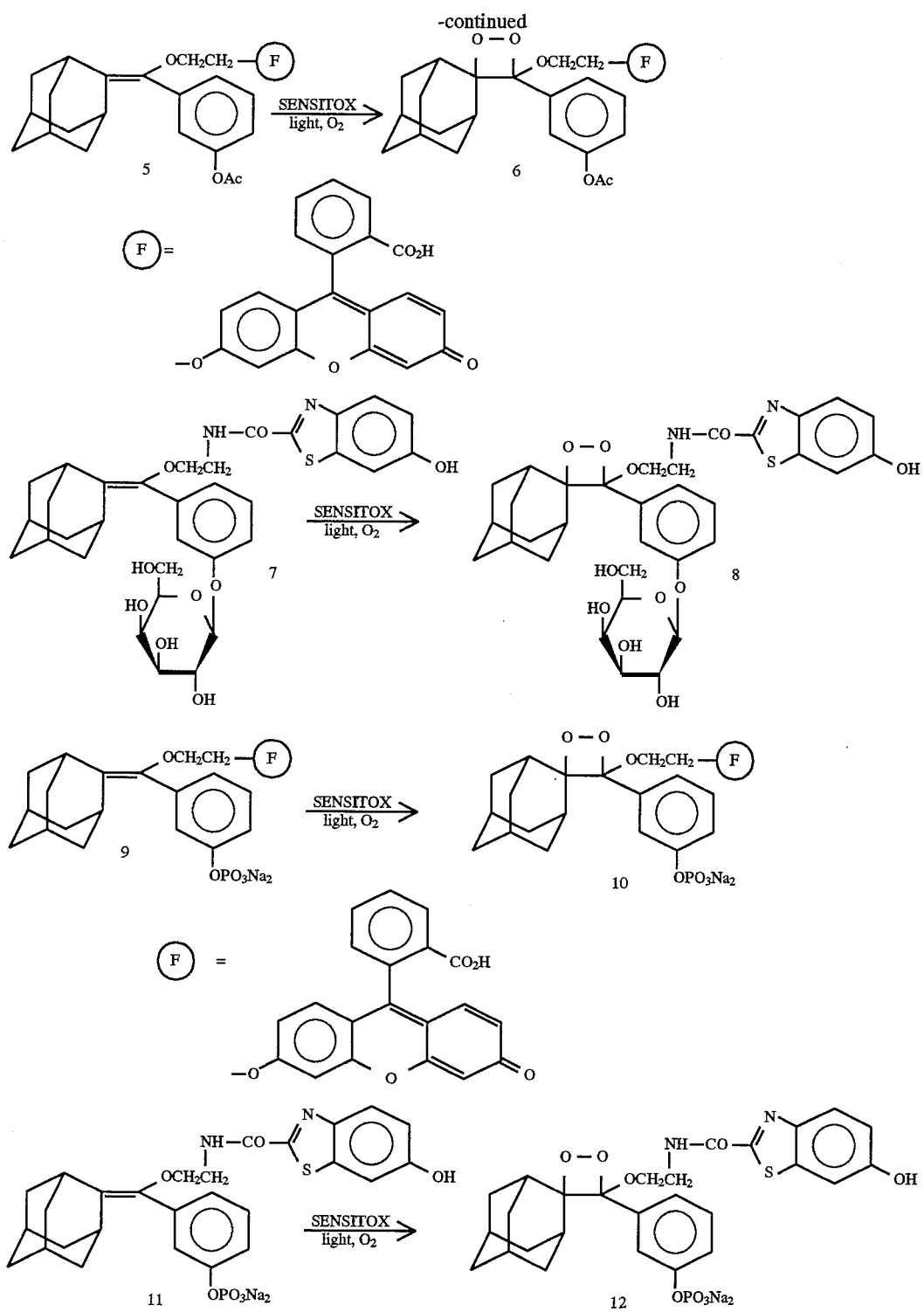

Instrumentation

Nuclear magnetic resonance (NMR) spectra were obtained on either a Nicolet NT300™ or a General Electric QE300™ spectrometer as solutions in $CDCl_3$ with tetramethylsilane as internal standard unless noted otherwise. Infrared (IR) spectra were obtained on either a Nicolet™ or a Beckman Acculab 8™ spectrometer. Mass spectra were obtained on either a Kratos™ or an AEI MS-90™ spectrometer. Ultraviolet and visible absorption spectra were obtained on a Varian Cary 219™ spectophotometer. Fluorescence spectra were recorded on a Spex Fluorolog™ spectrophotofluorometer. Chemiluminescence spectra were measured using the Spex Fluorometer. Chemiluminescence kinetic and quantum yield measurements were made with luminometers constructed in this laboratory. The instruments which use RCA A-31034A gallium-arsenide photomultiplier tubes cooled to −78° C. and Ortec photon-counting electronics are interfaced to Apple IIe™ and Macintosh™ computers. Elemental analyses were performed by Midwest Microlabs, Indianapolis. Melting points were measured in a Thomas Hoover™ capillary melting apparatus and are uncorrected. Precision weights were obtained on a Cahn model 4700™ electrobalance.

Materials o-Xylene was obtained from Burdick and Jackson Laboratories and used as received for kinetic and spectroscopic measurements. Dry DMF and DMSO were obtained by vacuum distillation from calcium hydride. Deuterium oxide, 1,4-dioxane-$d_8$, chloroform-d, and other chemical reagents were purchased from Aldrich Chemical Co. Samples of aryl esterase were purchased from Sigma Chemical Co. Silica, alumina, and the other solid supports were obtained from various commercial sources and used without further purification.

Syntheses of Alkenes

[(3-Hydroxyphenyl)methoxymethylene]adamantane(1a) was prepared as described in my previous application Ser. No. 224,681, filed Jul. 27, 1988. A 500-mL flask was fitted with a reflux condenser, a 125-mL addition funnel, and nitrogen line. The apparatus was dried by means of a hot air gun and nitrogen purging. Dry THF (40 mL) was added and the flask cooled in an ice bath. $TiCl_3$ (1.5 g, 10 mmol) was added rapidly followed by LAH (0.19 g, 5 mmol) in portions with stirring. The cooling bath was removed and the black mixture was allowed to warm to room temperature. Triethylamine (0.7 mL, 5 mmol) was added to the stirred suspension and refluxed for 15 min. After this period, a solution of methyl 3-hydroxybenzoate (152 mg, 1 mmol) and 2-adamantanone (300 mg, 2 mmol) in 20 mL of dry THF was added dropwise to the refluxing mixture over 15 min. Refluxing was continued for an additional 15 min after which the reaction was cooled to room temperature and diluted with 100 mL of distilled water. The aqueous solution was extracted with 3×50 mL portions of ethyl acetate. The combined organic layer was washed with water, dried over $MgSO_4$, and concentrated. Chromatography over silica with 15% ethyl acetate/hexane gave 240 mg (89 %) of 1a as a white solid: mp 133°–4° C.; $^1H$ NMR ($CDCl_3$) δ1.64–1.96 (m, 12H), 2.65 (s, 1H), 3.24 (s, 1H), 3.32 (s, 3H), 5.25 (s, 1H, OH exchange with $D_2O$ 6.70–7.30 (m, 4H); $^{13}C$ NMR ($CDCl_3$) δ28.45, 30.36, 32.36, 37.30, 39.18, 39.33, 57.82, 114.60, 116.16, 122.19, 129.24, 137.24, 155.62; MS m/e (rel intensity) 271 (20, M+1), 270 (100, M), 253 (7.3), 213 (35.1), 121 (41.7), 93 (9.4); Exact mass: calcd 270.1619, found 270.1616.

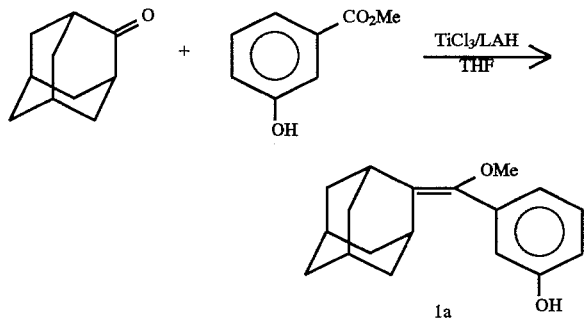

[(3-Acetoxyphenyl)methoxymethylene]adamantane(1b) was prepared as described in the previous application. Hydroxy alkene 1a (0.75 g, 2.8 mmol) was dissolved in 10 mL of $CH_2Cl_2$ and pyridine (5.2 g, 65.8 mmol) under $N_2$. The solution was cooled in an ice bath and a solution of acetyl chloride (2.6 g, 33 mmol) in 1 mL of $CH_2Cl_2$ was added dropwise via syringe. After 5 min at 0° C., TLC on silica with 20% ethyl acetate/hexane showed complete acetylation of 1a. After removal of the solvent, the solid residue was washed with 30 mL of ether. The ether was washed with 3×25 mL of water, dried over $MgSO_4$, and evaporated to dryness. The product was chromatographed on silica using 20% ethyl acetate/hexane affording 0.45 g of 1b as an oil: $^1H$ NMR ($CDCl_3$) δ1.79–1.96 (m, 12H), 2.27 (s, 3H), 2.66 (s, 1H), 3.26 (s, 1H), 3.29 (s, 3H), 6.99–7.36 (m, 4H); $^{13}C$ NMR ($CDCl_3$) δ20.90, 28.13, 30.07, 31.99, 36.99, 38.89, 39.01, 57.59, 120.34, 122.14, 126.55, 128.66, 132.19, 136.90, 142.59, 150.42, 169.04; MS m/e (rel intensity) 312 (100, M), 270 (25), 255 (19.3), 213 (20.7), 163 (12.2), 121 (30.7), 43 (30); IR (neat) 3006, 2925, 2856, 1725, 1600, 1438, 1362, 1218, 1100 $cm^{-1}$; Anal. Calcd. for $C_{20}H_{24}O_3$: C, 76.92; H, 7.69. Found: C, 76.96; H, 7.85.

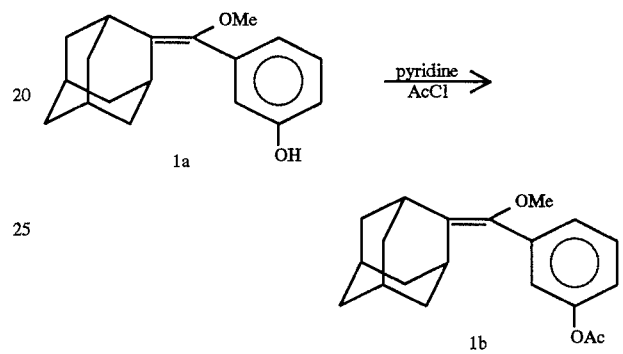

[(3-(β-D-Galactopyranosyl)phenyl)methoxymethylene]adamantane(1c).

[(3-Hydroxyphenyl)methoxymethylene]adamantane(1a) (0.462 g, 1.12 mmol) was dissolved in a minimum amount of acetone with a small amount 10M KOH. After stirring the solution for 15 min, a solution of 2,3,4,6-tetra-0-acetyl-β-D-galactopyranosyl bromide in acetone was mixed with alkene solution. The reaction was allowed to proceed overnight at room temperature. The acetone was then evaporated and the aqueous slurry was washed with water and extracted with ethyl acetate. The ethyl acetate fractions were combined and extracted with water, dried with $MgSO_4$, and evaporated to dryness. The solid product was recrystallized from a mixture of methylene/hexane to give 0.103 g (0.238 mmol, 62% ) of a pale yellow solid: $^1H$ NMR (dioxane-$d_8$) δ1.75–1.95 (m, 12H), 2.60 (s,1H), 2.79 (s,1H), 3.26 (s,3H), 3.62–3.81 (m,4H), 4.06 (d,1H), 4.37 (d,1H), 4.86 (d,1H), 6.93–7.27 (m, 4H); $^{13}C$ NMR (dioxane-$d_8$) δ13.59, 22.48, 28.45, 30.19, 31.47, 32.31, 37.13, 38.93, 39.08, 56.91, 61.42, 68.92, 71.39, 73.94, 75.84, 100.87, 115.28, 117.11, 123.01, 128.93, 131.03, 136.98, 143.74, 157.56; MS m/e (rel. intensity) 432 (15), 270 (100), 213 (10), 101(17), 83 (13), 59 (47), 43(96).

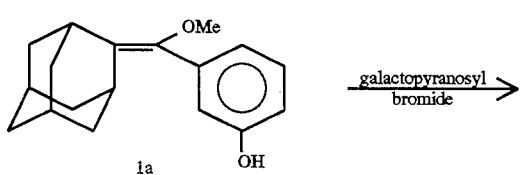

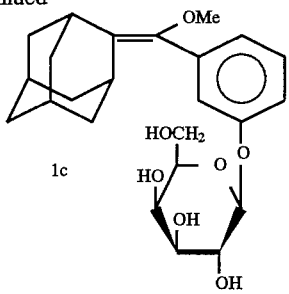

2-Cyano-6-hydroxybenzothiazole.

Dry pyridinium hydrochloride (34.0 g, 0.294 mol) and 2-cyano-6-methoxy-benzothiazole (Aldrich Chemical Co., 3.0 g, 0.016 mol) were added into a 500 mL round bottom flask which was preheated in an oil bath at 100° C. The bath temperature was increased to 190° C. and the reaction mixture was refluxed at this temperature for 2 h. After the completion of reaction, it was cooled to room temperature to obtain a yellow solid which was dissolved in methanol. Silica was added to this solution and evaporated to dryness. This material was then chromatographed using 30% ethyl acetate/hexane to obtain 2.7 g of the product as a white solid (95%): mp 120° C.; $^1$H NMR (CD$_3$OD) δ5.68 (bs, 1H), 8.02–8.82 (m, 3H); $^{13}$C NMR (CD$_3$OD) δ106.96, 114.26, 119.59, 126.53, 133.83, 138.93, 147.25, 160.23; MS m/e (rel intensity) 176 (100), 151 (3), 124 (5), 96 (15), 85 (4), 69 (7), 57 (5); Exact mass: calcd 176.0044, found 176.0047.

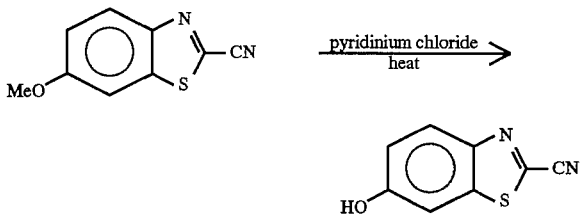

Methyl 6-hydroxy-2-benzothiazoate.

Dry methanol (30 mL) was saturated with HCl by passing dry HCl gas for 10 min. To this solution was added 2-cyano-6-hydroxybenzothiazole (0.475 g, 0.0023 mol). The resulting yellow solution was stirred at room temperature for 4 days. After the end of this period, the product crystallized out of the solution as a yellow solid which was obtained by vacuum filtration, washed with water and dried to yield the product as a white solid (0.565 g, 100%): mp 200° C.; $^1$H NMR (CD$_3$OD) δ3.92 (s, 3H), 7.02–7.86 (m, 3H); $^{13}$C NMR (CD$_3$OD) δ52.38, 105.88, 117.66, 124.98, 138.43, 146.18, 154.34, 158.12, 160.12; MS m/e (rel intensity) 209 (82), 178 (25), 151 (100), 123 (6), 106 (9), 95 (12), 85 (5), 69 (10), 59 (10), 51 (6), 45 (11); Exact mass: calcd 209.0146, found 209.0149.

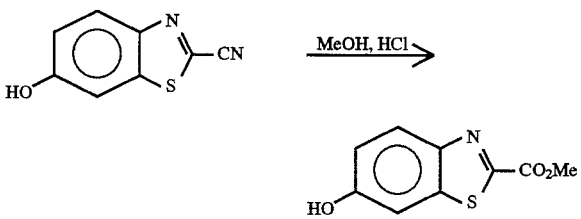

Methyl (6-tert-butyldimethylsilyloxy)-2-benzothiazoate.

To a solution of methyl 6-hydroxy-2-benzathiazoate (1.5 g, 0.007 mol) and tert-butyldimethylsilyl chloride (0.7 g, 0.011 mol) in 5 mL of dry DMF, was gradually added imidazole (0.980 g, 0.014 mol). The solution was then stirred overnight. TLC analysis (silica gel, 20% ethyl acetate/hexane) showed clean conversion to a new material. The solution was poured into 25 mL of water and extracted with 3×25 mL of ether. The combined ether solutions were dried over anhydrous MgSO$_4$. Evaporation of solvent gave an oil which was chromatographed on silica using 10% ethyl acetate/hexane to give 2.2 g (96%) of the product as a colorless liquid: $^1$H NMR (CDCl$_3$) δ0.255 (s, 6H), 1.01 (s, 9H), 4.06 (s, 3H), 7.04–8.07 (m, 3H); $^{13}$C NMR (CDCl$_3$) δ–5.07, 17.53, 24.95, 52.64, 110.77, 120.95, 125.45, 137.77, 147.61, 154.98, 155.15, 160.35.

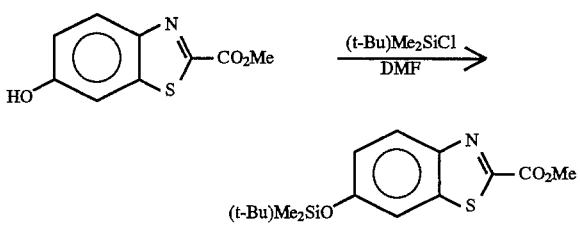

2-Chloroethyl 3-hydroxybenzoate.

A solution of 3-hydroxybenzoic acid (15.0 g, 0.11 mol) in 2-chloroethanol (70 mL, 1.0 mol) and 1 mL of concentrated sulfuric acid was refluxed for overnight. TLC analysis (silica gel/20% ethyl acetate/hexane) showed clean conversion to a new material. The excess chloroethanol was removed by evaporation to obtain a brown solution which was dissolved in ethyl acetate and washed with water. The organic layer was dried with MgSO$_4$ and concentrated to obtain 21.0 g of the product as a white solid: mp 50° C.; $^1$H NMR (CDCl$_3$) δ3.81 (t, 2H, J=5.9 MHz), 4.57 (t, 2H, J=5.9 MHz), 4.77 (s, 1H), 7.06–7.66 (m, 4H); $^{13}$C NMR (CDCl$_3$) δ41.52, 64.75, 116.43, 120.77, 121.98, 129.80, 130.71, 156.04, 166.57; MS m/e (rel intensity) 200 (26), 138 (59), 121 (100), 93 (31), 65 (21), 39 (12); Exact mass: calcd 200.0240, found 200.0242.

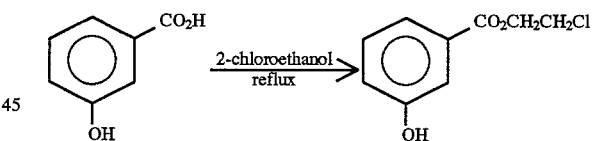

2-Chloroethyl 3-(tert-butyldimethylsilyloxy)benzoate.

To a solution of 2-chloroethyl 3-hydroxybenzoate (4.0 g, 0.02 mol) and tert-butyldimethylsilyl chloride (4.5 g, 0.029 mol) in 5 mL of dry DMF was gradually added imidazole (92.7 g, 0.04 mol). The solution was then stirred overnight. TLC analysis (silica gel, 20% ethyl acetate/hexane) showed clean conversion to a new material. The solution was poured into a 25 mL of water and extracted with 3×25 mL of ether. The combined ether solutions were dried over anhydrous MgSO$_4$. Evaporation of the solvent gave an oil which was chromatographed on silica using 10% ethyl acetate/hexane to give the product quantitatively as a colorless liquid: $^1$H NMR (CDCl$_3$) δ0.218 (s, 6H), 0.994 (s, 9H), 3.81 (t, 2H, J=5.7 MHz), 4.56 (t, 2H, J=5.7 MHz), 7.05–7.65 (m, 4H); $^{13}$C NMR (CDCl$_3$) δ–4.97, 17.66, 25.12, 41.06, 63.91, 120.61, 122.19, 124.60, 128.95, 130.53, 155.31, 165.35; MS m/e (rel intensity) 314 (14), 257 (9), 235 (9), 213 (100), 185 (6) 149 (7), 135 (10), 120 (6), 93 (13), 83 (6), 69 (9), 55 (9); Exact mass: calcd 314.1104, found 314.1110.

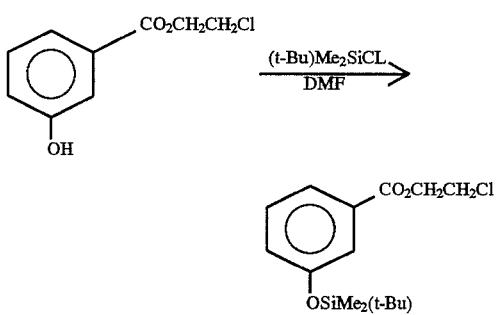

[(3-tert-Butyldimethylsilyloxylphenyl)(2-chloroethyl) methylene]adamantane.

A 100 mL three-necked flask fitted with a reflux condenser, was dried by means of a hot air gun and nitrogen purging. This was charged with dry THF 200 mL and cooled in an ice-bath. Titanium trichloride (24.5 g, 0.16 mol) followed by lithium aluminum hydride (3.0 g, 0.08 mol) in portions with vigorous stirring. The cooling bath was removed and the black mixture was allowed to warm to room temperature. Triethylamine (15 mL) was added dropwise and the reaction mixture was refluxed for 1 h. A solution of 2-chloroethyl 3-(tertbutyldimethylsilyloxy) benzoate (5.0 g, 0.015 mol) and 2-adamantanone (7.1 g, 0.05 mol) was added dropwise to the refluxing mixture over a 1 h period. TLC analysis (silica gel 10% ethyl acetate/hexane) after 1 h of refluxing showed conversion to a new material. The reaction mixture was cooled, extracted with hexane. After the evaporation of solvent, the crude material was chromatographed using 3% ethyl acetate/hexane to give 5.0 g (74%) of the product as a white oil: $^1$H NMR (CDCl$_3$) δ0.194 (s, 6H), 0.982 (s, 9H), 1.78–1.98 (m, 12H), 2.65 (s, 1H), 3.34 (s, 1H), 3.55 (t, 2H, J=5.7 MHz), 3.66 (t, 2H, J=5.7 MHz), 6.85–7.29 (m, 4H); $^{13}$C NMR (CDCl$_3$) δ–4.46, 18.21, 25.66, 28.28, 30.20, 32.39, 38.94, 39.20, 42.61, 68.95, 119.62, 121.04, 122.50, 129.09, 132.78, 136.40, 141.11, 155.49; MS m/e (rel intensity) 432 (100), 331 (22), 235 (13), 199 (10), 151 (19), 105 (17), 73 (44), 57 (14); Exact mass: calcd 432.2251, found: 432.2247.

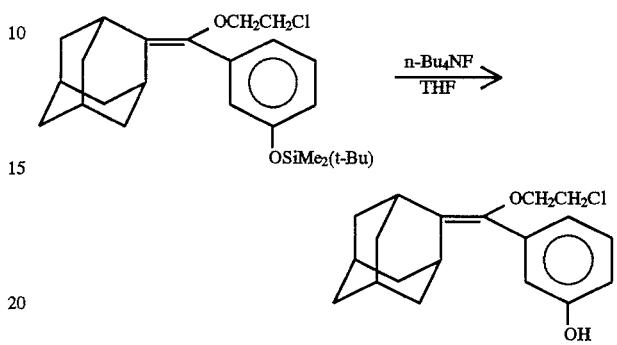

[(2-Chloroethoxy)(3-hydroxyphenyl)methylene] adamantane.

To a stirred solution of the tert-butyldimethylsilyl protected-alkene shown above (2.0 g, 0.004 mol) in 5 mL of THF was added tetrabutylammonium fluoride trihydrate (1.4 g, 0.004 mol) and the resulting solution was stirred for 10 min. TLC analysis (silica gel, 20% ethyl acetate/hexane) indicated conversion to a new material. After evaporation of solvent, the crude product was washed with water and taken up in ether. The organic layer was dried over MgSO$_4$ and evaporated to dryness. The oily material was chromatographed on silica gel using 20% ethyl acetate/hexane to give 1.3 g (100%) of the product: $^1$H NMR (CDCl$_3$) δ1.81–1.96 (m, 12H), 2.67 (s, 1H), 3.34 (s, 1H), 3.55 (t, 2H, J=5.6 MHz), 3.69 (t, 2H, J=5.6 MHz), 6.77–7.19 (m, 4H); $^{13}$C NMR (CDCl$_3$) δ28.21, 30.24 32.35, 37.08, 38.92, 39.19, 42.55, 69.05, 114.76, 116.05, 12.1.92, 129.31, 133.41, 136.62, 140.77, 155.64; MS m/e (rel intensity) 318 (100), 227 (19), 213 (24), 121 (92), 107 (29), 93 (37), 69 (21), 55 (36), 41 (40); Exact Mass: calcd 318.1386, found 318.1383.

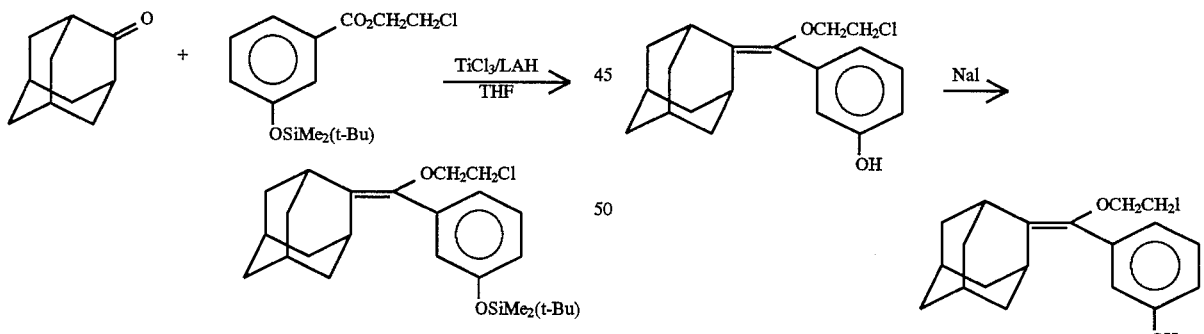

[(3-Hydroxyphenyl)(2-iodoethoxy)methylene]adamantane.

Sodium iodide (14.0 g, 0.09 mol) and [(2-chloroethoxy) (3-hydroxyphenyl)methylene]adamantane (3.0 .g, 0.009 mol) were dissolved in dry acetone and refluxed for 6 days. The reaction was followed by TLC analysis (silica gel, 10% ethyl acetate/hexane) and after the completion of reaction, solvent was evaporated to obtain a white solid. This solid was washed with methylene chloride several times and the combined organic layers were again washed with water. The organic layer was dried over MgSO$_4$ and concentrated to give 3.8 g (100%) of product as an oily material: $^1$H NMR (CDCl$_3$) δ1.78–1.97 (m, 12H), 2.64 (bs, 1H), 3.19 (t, 2H, J=7.1 MHz), 3.35 (bs, 1H), 3.69 (t, 2H, J=7.1 MHz), 6.75–7.21 (m, 4H); $^{13}$C NMR (CDCl$_3$) δ2.40, 28.13, 30.41, 32.33, 36.99, 38.86, 39.09, 69.74, 114.86, 116.00, 121.79, 129.28, 133.37, 136.42, 140.51, 155.66. MS m/e (rel intensity) 410 (42), 256 (19), 227 (75), 155 (18), 121 (100), 107 (32), 93 (28), 79 (14), 65 (16); Exact mass: calcd 410.0744, found: 410.0744.

[(2-Aminoethoxy)(3-hydroxyphenyl)methylene] adamantane.

A solution of [(3-hydroxyphenyl)(2-iodoethoxy) methylene]adamantane (3.0 g, 0.01 mol) in a minimum amount of THF was added into 10 mL of liquid ammonia in a sealed tube which was kept in dry ice. After sealing the tube this was heated at 40° C. in an oil bath for 17 h. The reaction mixture was cooled down and solvent evaporated to obtain a white solid. This material was extracted with methylene chloride. The combined organic layers were washed with water, dried over MgSO$_4$, and concentrated to give 2.0 g (90%) of the product as a white solid: mp 55° C.; ¹H NMR (CDCl₃) δ1.77–1.96 (m, 12H), 2.68 (bs, 1H), 2.85 (t, 2H, J=4.8 MHz), 3.23 (bs, 1H), 3.48 (t, 2H, J=4.8 MHz), 4.46 (bs, 2H), 6.70–7.17 (m, 4H); ¹³C NMR (CDCl₃) δ28.16, 30.28, 32.19, 36.99, 38.88, 39.04, 41.33, 70.45, 114.97, 116.17, 120.63, 129.02, 131.89, 136.69, 141.79, 156.86; MS m/e (rel intensity) 299 (10), 256 (100), 239 (5), 199 (6), 135 (12), 121 (27), 93 (12), 77 (5). Exact mass: calcd 299:1885, found: 299.1891.

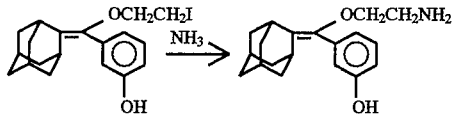

{[2-(N-(6-tert-Butyldimethylsilyloxybenzothiazole-2-carbonyl)amino)ethoxy][3-hydroxyphenyl]methylene}adamantane.

Methyl 6-tert-butyldimethylsilyloxy-2-benzothiazoate (1.2 g, 0.004 mol) and [(2-aminoethoxy)(3-hydroxyphenyl) methylene]adamantane (3.3 g, 0.011 mmol) were dissolved in dry methanol and refluxed gently with trace of NaHCO₃. After 4 days, completion of the reaction was indicated by NMR. After evaporation of the solvent, the crude material was chromatographed using silica gel and 20% ethyl acetate/hexane to yield 60 mg (88%) of the product as a white solid: mp105° C.; ¹H NMR (CDCl₃) δ0.158 (s, 6H), 0.945 (s, 9H), 1.79–1.97 (m, 12H), 2.65 (bs, 1H), 3.32 (bs, 1H), 3.64 (m, 4H ), 6.73–7.38 (m, 7H), 7.76 (bs, 1H), 7.95 (t, 1H); ¹³C NMR (CDCl₃): δ–4.59, 15.02, 25.51 28.16, 30.34, 32.26, 37.00, 38.39, 39.03, 39.89, 67.42, 106.91, 117.34, 119.54, 120.96, 122.32, 124.96, 129.13, 136.29, 138.77, 141.54, 146.94, 155.39, 156.46, 159.59, 160.34, 160.49.

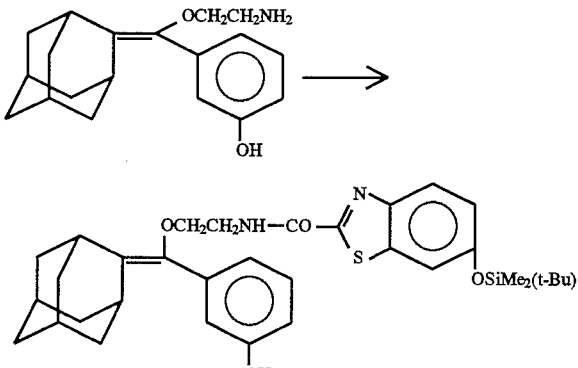

{[3-Acetoxyphenyl][2-(N-(6-tert-butyldimethylsilyloxybenzo thiazole-2-carbonyl)amino) ethoxy]methylene}adamantane.

The corresponding hydroxy alkene shown above (60 mg, 0.01 mmol) was dissolved in 1 mL of methylene chloride and 300 µL of pyridine under nitrogen. This solution was cooled in an ice bath and 36 µL of acetyl chloride (39 mg, 0.5 mmol) was added dropwise via a syringe. After stirring this solution for 1 hr at 0° C., TLC (silica gel, 20% ethyl acetate/hexane) indicated completion of the reaction. After removal of solvent in vacuo, the solid residue was dissolved in ether and washed with water. The ether layer was dried over MgSO₄ and concentrated to obtain an oily material. This material was chromotographed on silica using 15% ethyl acetate and hexane to obtain an inseparable mixture (9:1) of the NH alkene and N-acetylated alkene. Spectral data for the NH alkene: ¹H NMR (CDCl₃) δ0.165 (s, 6H), 0.95 (s, 9H), 1.8–1.97 (m, 12H), 2.17 (s, 3H), 2.36 (bs, 1H), 2.65 (bs,1H), 3.34 (bs,1H), 3.65 (m, 4H), 6.73–8.07 (m, 7H), 7.79 (bs, 1H); ¹³C NMR (CDCl₃) δ–4.48, 18.16, 21.05, 25.63, 28.30, 30.45, 32.44, 37.12, 39.02, 39.16, 39.93, 67.56, 115.01, 119.61, 121.08, 121.52, 122.41, 124.92, 129.19, 132.19, 136.48, 137.86, 141.72, 149.28, 150.83, 155.52, 159.64, 164.12, 169.21.

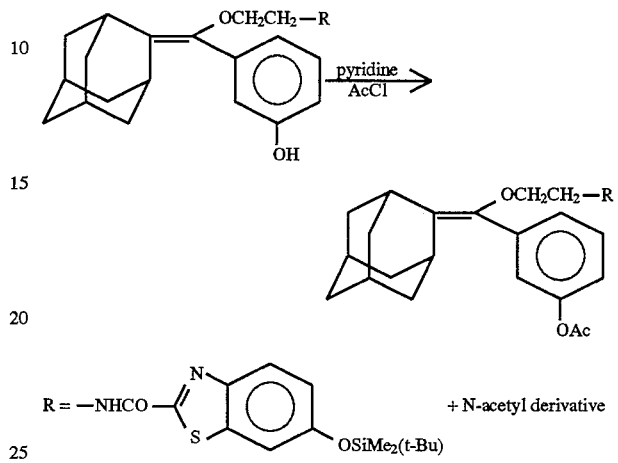

{[2-(N-Acetyl-N-(6-hydroxybenzothiazole-2-carbonyl)amino)ethoxy][3-hydroxyphenyl]methylene}adamantane (3a) and {[3-Acetoxyphenyl][2-(N-acetyl-N-(6-hydroxybenzo thiazole-2-carbonyl)amino)ethoxy]methylene}adamantane(3b).

To a cold solution of the above mixture (100 mg, 0.16 mmol) in 1 mL of THF was added a solution of tetrabutylammonium fluoride trihydrate (49 mg, 0.16 mmol) in 0.5 mL of THF via a syringe. TLC analysis after the addition (silica gel, 1:1 ethyl acetate/hexane) showed the formation of three products. After the evaporation of the solvent, the crude product was washed with water, dried over MgSO₄, and concentrated. The crude oily material was chromatographed on silica using ethyl acetate and hexane to obtain three products. The first product was obtained with 25% ethyl acetate/hexane and identified as alkene (3b): ¹H NMR (CDCl₃) δ1.81–1.98 (m, 12H), 2.18 (s, 3H), 2.37 (s, 3H), 2.68 (bs, 1H), 3.34 (bs, 1H), 3.65 (m, 4H), 6.97–8.79 (m, 7H), 7.77 (bs, 1H); ¹³C NMR (CDCl₃) δ20.96, 21.04, 28.23, 30.55, 32.34, 37.07, 39.03, 39.16, 39.94, 67.81, 104.9, 115.03, 120.77, 121.54, 122.36, 124.88, 126.65, 129.08, 131.34, 133.43, 133.53, 136.69, 141.04, 149.31, 150.68, 159.60, 169.21.

The second product was obtained with 35% ethyl acetate/hexane and was found to be {[2-(N-acetyl-N-(6-hydroxybenzothiazole-2-carbonyl)amino)ethoxy][3-hydroxyphenyl]methylene}adamantane (3a): ¹H NMR (CDCl₃) δ1.80–1.96 (m, 12H), 2.18 (s, 3H), 2.67 (bs, 1H), 3.33 (bs, 1H), 3.65 (m, 4H), 6.74 (bs, 6.96–7.92 (m, 7H), 7.79 (bs, 1H); ¹³C NMR (CDCl₃) δ20.97, 28.22, 30.53, 32.35, 37.07, 39.01, 39.14, 39.97, 67.79, 107.09, 117.16, 120.75, 122.35, 125.13, 126.71, 129.10, 133.50, 136.72, 138.86, 140.98, 147.39, 150.65, 155.72, 160.34, 160.43, 169.36. The third product was identified as {[2-(N-(6-hydroxybenzothiazole-2-carbonyl)amino)ethoxy][3-hydroxyphenyl]methylene}adamantane

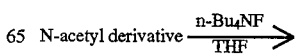

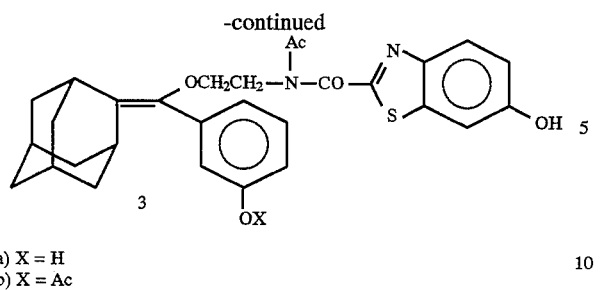

(a) X = H
(b) X = Ac

[(3-Acetoxyphenyl)(2-chloroethoxy)methylene] adamantane.

The corresponding hydroxy alkene (1 g, 3.13 mmol) was dissolved in 15 mL of methylene chloride and pyridine (5 mL, 63 mmol) under $N_2$. The solution was cooled in an ice bath and a solution of acetyl chloride (0.25 g, 3.13 mmol) in 1 mL of methylene chloride was added dropwise by a syringe. A white precipitate formed. After two h at 0°–5° C., TLC with 10% ethyl acetate/hexane) showed complete acetylation. After removal of the solvent in vacuo, the solid residue was washed with 100 mL of hexane. The hexane was washed with 2×50 mL of water, dried over $MgSO_4$ and evaporated to dryness. The oily material was chromatographed on silica using 10% ethyl acetate/hexane to give the product (0.91 g, 2.52 mmol, 80%): $^1H$ NMR ($CDCl_3$) δ1.70–2.00 (m, 12H), 2.30 (s,3H), 2.67 (s,1H), 3.50 (s 1H), 3.54–3.58 (t, 2H), 3.67–3.69 (t, 2H), 7.00–7.40 (m, 4H); $^{13}C$ NMR ($CDCl_3$) δ21.11, 28.19, 30.27, 32.28, 37.07, 38.92, 39.17, 42.62, 69.22, 120.76, 122.32, 126.70, 129.02, 133.93, 136.64, 140.40, 150.59, 169.28.

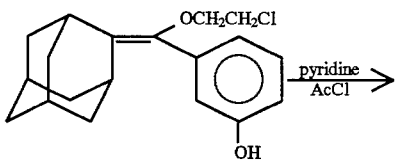

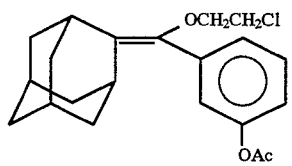

[(3-Acetoxyphenyl)(2-iodoethoxy)methylene]adamantane.

To a solution of the chloroalkene (0.4 g, 2.49 mmol) in 10 mL of dry acetone was slowly added anhydrous sodium iodide. The solution was refluxed for four days in the dark. TLC analysis on silica with 10% ethylacetate/hexane showed clean conversion to a new, less polar material. Evaporation of the solvent gave a white solid which was washed with hexane. The hexane solution was evaporated to give the product as a colorless oil (1.11 g, 2.45 mmol, 98%): $^1H$ NMR ($CDCl_3$) δ1.70–2.00 (m, 12H), 2.30 (s, 3H), 2.65 (s, 1H), 3.17–3.21 (t, 2H), 3.36 (s, 1H), 3.66–3.70 (t, 2H), 6.99–7.4 (m, 4H); $^{13}C$ NMR ($CDCl_3$) δ21.14, 28.21, 30.51, 32.33, 37.10, 38.96, 39.18, 69.94, 116.32, 120.79, 122.34, 126.72, 129.04, 133.93, 136.63, 140.39, 150.60, 169.28.

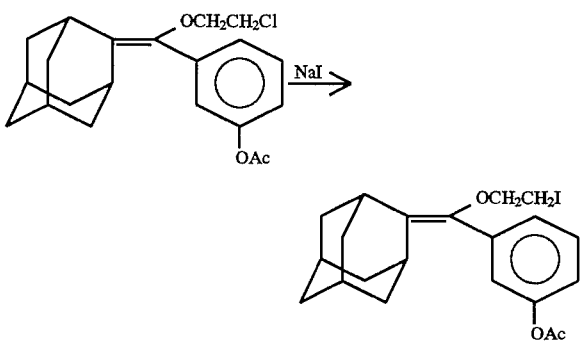

[(3-Acetoxyphenyl)(2-(O-fluorescein)ethoxy)methylene] adamantane(5).

The iodoalkene (1 g, 2.21 mmol), fluorescein (1.47 g, 4.42 mmol), and silver oxide (5 g, 21.6 mmol) were placed in a 50 mL round-bottom flask containing 20 mL of dry benzene. The resulting yellow suspension was refluxed in the dark for 24 h. After cooling, the solid silver oxide and silver iodide were filtered off and the filtrate was evaporated to dryness under vacuum. The yellow solid was chromatographed over silica with 20% ethyl acetane/benzene to give the pure product as a yellow solid (1.09 g, 1.66 mmol, 75%): $^1H$ NMR (p-dioxane-$d_8$) δ1.69–1.95 (m, 12H), 2.22 (s, 3H), 2.64 (s, 1H), 3.33 (s, H), 3.7–3.79 (s, 2H), 4.00–4.1 (s, 2H), 6.40–8.20 (m, 14H); $^{13}C$ NMR (p-dioxane-$d_8$) 20.63, 28.48, 30.85, 33.06, 37.64, 39.37, 39.68, 67.94, 67.67, 82.76, 101.95, 103.12, 112.56, 112.73, 112.92, 121.44, 123.17, 124.39, 125.40, 127.21, 127.73, 128.93, 129.52, 129.72, 129.97, 133.49, 135.20, 137.53, 141.81, 151.74, 152.91, 153.01, 154.48, 159.59, 161.29, 169.10.

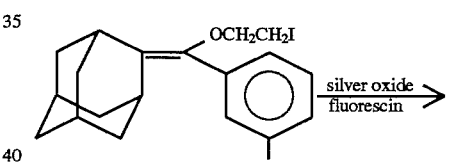

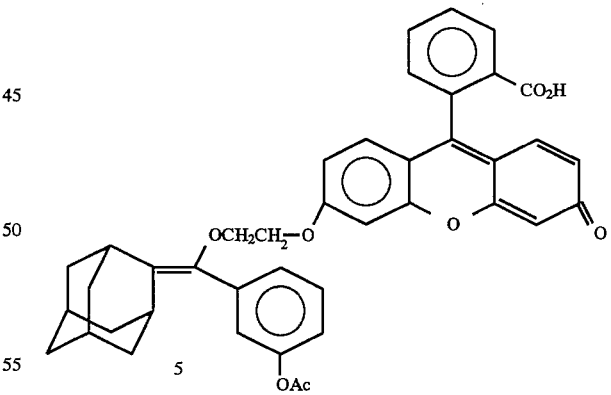

[(2-Aminoethoxy)(3-β-D-galactopyranosylphenyl) methylene]adamantane. Acetobromo-α-D-galactose (5 g, 1.2 mmol) was slowly added to a solution of [(3-hydroxyphenyl)(2-iodoethoxy)methylene]adamantane (1 g, 0.24 mmol) in 1:1 5N KOH and acetone (5 mL). This mixture was stirred at room temperature for 10 min. TLC analysis (silica gel, 50% ethyl acetate/hexane) indicated formation of five new compounds due to the partial deacetylation. After evaporation of the solvent, the crude material was washed with water and evaporated to dryness. This material was dissolved in a minimum amount of THF and added into 20 mL of liquid ammonia in a tube. After sealing the tube, this solution was heated at 40° C. in an oil bath for 17 h. The reaction mixture was cooled down and the solvent evaporated to obtain a white solid which was extracted with ethyl acetate. The combined organic layers were washed with water, dried over MgSO$_4$, and concentrated to give 800 mg (73%) of the product as a white solid. This material was carried on to the next step without further purification.

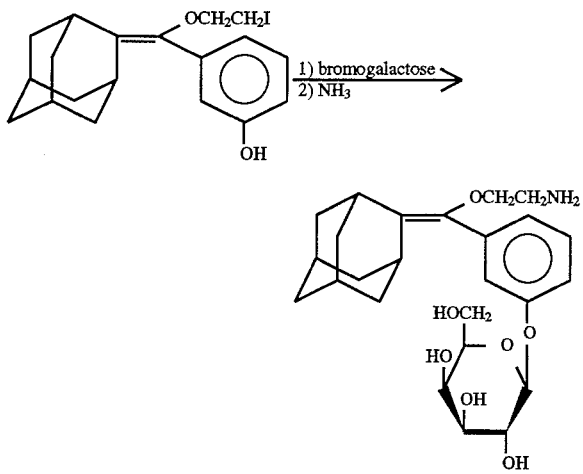

{[2-(N-(6-hydroxybenzothiazoate-2-carbonyl)amino) ethoxy][3-β-D-galactopyranosyl phenyl]methylene}adamantane(7).

Methyl 6-tert-butyldimethylsilyloxy-2-benzothiazoate (363 mg, 0.17 mmol) and the product from previous reaction (800 mg, 0.17 mmol) were dissolved in dry methanol and refluxed gently with trace of NaHCO$_3$. After evaporation of the solvent, the crude material was washed with water and taken up in ethyl acetate. This solution was concentrated to give a white solid which was chromatographed using silica gel and 100% acetone to yield 800 mg (80%) of 7 as a white solid: mp 65° C.; $^1$H NMR (acetone-d$_6$) δ1.65–1.88 (m, 12H), 2.6 (s, 1H), 3.3 (s, 1H), 3.6–4.01 (m, 10H), 4.94 (d, 1H), 6.5 (bs, 1H), 6.91–7.89 (m, 7H), 8.19 (s, 1H); $^{13}$C NMR (acetone-d$_6$) δ28.19, 28.90, 30.16, 30.22, 32.24, 32.49, 36.83, 38.65, 38.82, 39.53, 61.25, 67.35, 68.82, 71.16, 73.73, 75.27, 101.11, 106.79, 115.79, 117.06, 117.14, 122.82, 124.91, 129.03, 131.49, 136.49, 138.49, 141.96, 146.77, 157.10, 157.60, 159.96, 160.45.

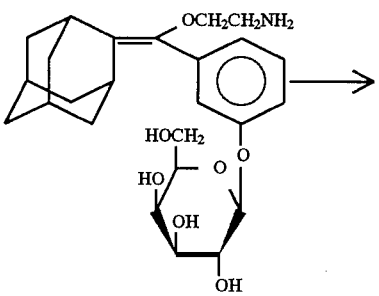

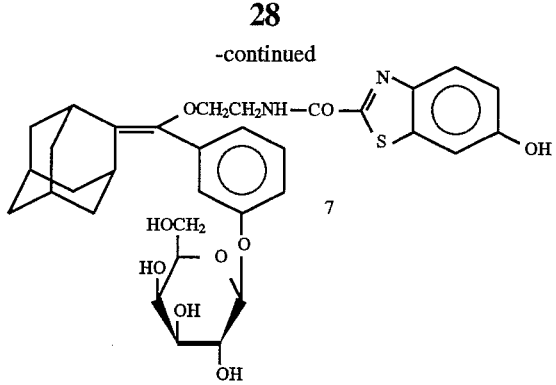

[(3-Phosphatephenyl)(2-(O-fluorescein)ethoxy) methylene]adamantane(9) and {[2-(N-(6-hydroxybenzothiazoate-2-carbonyl)amino)ethoxy][3-phosphatephenyl]methylene}adamantane, disodium salt(11) are prepared from the corresponding hydroxy-substituted compounds using phosphorylation procedures described in my previous application Ser. No. 224,681, filed Jul. 27, 1988.

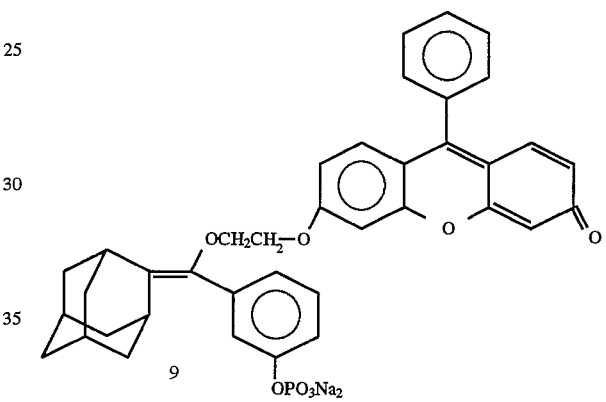

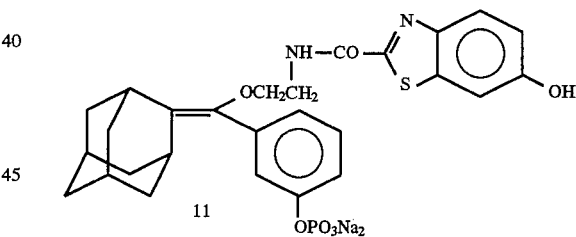

Preparation of 1,2-Dioxetanes

Photooxygenation procedure. Typically a 5–10 mg sample of the alkene was dissolved in 5 mL of methylene chloride in the photooxygenation tube. Approximately 40 mg of polystyrene-bound Rose Bengal (Sensitox I) [reference to this type of sensitizer: A. P. Schaap, A. L. Thayer, E. C. Blossey, and D. C. Neckers, *J. Amer. Chem. Soc.*, 97, 3741 (1975)] was added and an oxygen bubbler connected. Oxygen was passed slowly through the solution for 5 min and the apparatus immersed in a half-silvered Dewar flask containing dry ice/2-propanol. The sample was irradiated with a 1000 W high pressure sodium lamp (General Electric Lucalox) and a UV cutoff filter while oxygen was bubbled continuously. Progress of the reaction was monitored by TLC. A spot for the highly stable dioxetanes could usually be detected and had a $R_f$ slightly less than that of the alkene. The adamantyl-substituted dioxetanes were filtered at room temperature, evaporated on a rotary evaporator, and recrystallized from a suitable solvent.

4-(3-Hydroxyphenyl)-4-methoxyspiro[1,2-dioxetane-3,2'-adamantane](2a).

Hydroxy alkene 1a (100 mg) was irradiated with a 1000 W sodium lamp in 8 mL of methylene chloride at −78° C. in the presence of Sensitox. The alkene and dioxetane on TLC using 20% ethyl acetate/hexane exhibit the same $R_f$ value. Therefore, the reaction was stopped when a trace of the cleavage product began to appear. The sensitizer was removed by filtration and the solvent evaporated. $^1$H NMR was used to check that all of the starting material had been oxidized. Dioxetane 2a was recrystallized from pentane/benzene to give a white solid: mp 135° C.: $^1$H NMR (CDCl$_3$) δ1.04–2.10 (m, 12H), 2.21 (s, 1H), 3.04 (s, 1H), 3.24 (s, 3H), 6.48 (s, 1H, OH exchange with D$_2$O), 6.93–7.30 (m, 4H). $^{13}$C NMR (CDCl$_3$) δ25.81, 25.95, 31.47, 31.57, 32.27, 32.86, 33.07, 34.58, 36.30, 49.83, 95.88, 112.08, 116.46, 129.34, 136.1, 156.21.

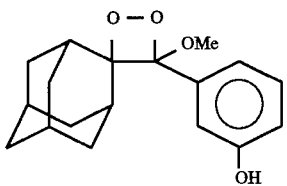

2a 4-(3-Acetoxyphenyl)-4-methoxyspiro[1,2-dioxetane-3,2'-adamantane](2b).

Alkene 1b (140 mg 0.45 mmol) was photooxygenated in 30 mL of methylene chloride at −78° C. with a 1000 W sodium lamp using 400 mg of Sensitox. TLC analysis on silica gel with 20% ethyl acetate/hexane) showed clean conversion to a more polar material in 2.5 h. Filtration and removal of solvent produced 2b as an oil: $^1$H NMR (CDCl$_3$) δ0.90–1.90 (m, 12H), 2.15 (2, 1H), 2.31 (s, 3H), 3.03 (s, 1H), 3.23 (s, 3H), 3.61–7.45 (m, 4H): $^{13}$C NMR (CDCl$_3$) δ21.00, 25.82, 25.97, 31.50, 31.65, 32.21, 32.80, 33.09, 34.71, 36.32, 49.92, 95.34, 111.50, 122.58, 129.16, 136.42, 150.72, 169.11.

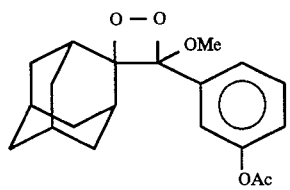

2b 4-(3-β-D-Galactopyranosylphenyl)-4-methoxyspiro[1,2-dioxetane-3,2'-adamantane](2c).

Alkene 1c (0.018 g, 0.042 mmol) was photooxygenated in 3 mL of dioxane-d$_8$ at 0° C. using Sensitox. The reaction was complete after 20 min of irradiation using the 1000 W sodium lamp. Spectral data for 2c: $^1$H NMR (dioxane-d$_8$) δ1.593–1.820 (m, 12H), 2.091 (s,1H), 2.517 (s, 1H), 3.160 (s, 3H), 3.670–3.854 (m,4H), 4.147 (d, 1H), 4.422 (d,1H), 4.846 (d,1H), 7.078–7.369 (m, 4H); $^{13}$C NMR (dioxane-d$_8$) δ26.209, 26.115, 31.459, 31.753, 32.890, 33.300, 34.643, 36.332, 49.227, 61.277, 68.803, 71.409, 73.856, 75.768, 75.806, 94.558, 101.099, 101.331, 111.457, 117.066, 129.246, 136.736, 154.682.

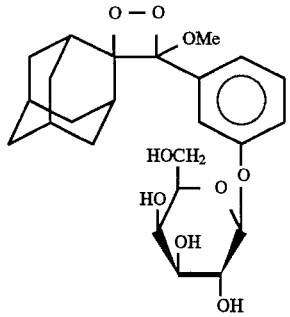

2c 4-(2-(N-Acetyl-N-(6-hydroxybenzothiazole-2-carbonyl)amino)ethoxy)-4-(3-hydroxy phenyl)spiro[1,2-dioxetane-3,2-adamantane](4a).

Alkene (3a) (25 mg 0.045 mmol) was photooxygenated in 4 mL of methylene chloride/acetone (1:1) at −78° C. with a 1000 W sodium lamp using 75 mg of Sensitox. TLC analysis (silica gel, 50% ethyl acetate/hexane) showed clean conversion to a more polar material in 90 min. Filtration and removal of solvent gave a white solid as the product (4a): $^1$H NMR (CDCl$_3$) δ1.56–186 (m, 12H), 2.23 (bs, 1H), 2.36 (s, 3H), 3.11 (bs, 1H), 3.58–3.79 (m, 4H), 7.15–8.08 (m, 7H).

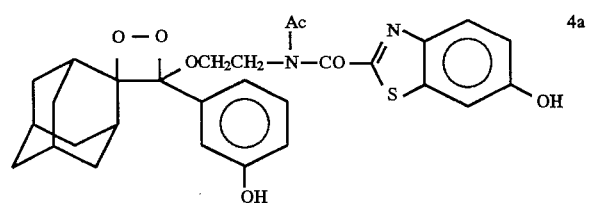

4a 4-(3-Acetoxyphenyl)-4-(2-(N-acetyl-N-(6-hydroxybenzothiazole-2-carbonyl)amino)ethoxy)spiro[1,2-dioxetane-3,2'-adamantane](4b)

Alkene (3b) (25 mg 0.042 mmol) was photooxygenated in 4 mL of methylene chloride at −78° C. with a 1000 W sodium lamp using 75 mg of Sensitox. TLC analysis (silica gel, 50% ethyl acetate/hexane) showed clean conversion to a more polar material in 50 min. Filtration and removal of solvent gave the product (4b) as a white solid: $^1$H NMR (CDCl$_3$) δ1.59–1.86 (m, 12H), 2.16 (bs, 1H), 2.21 (s, 3H), 3.12 (bs, 1H), 3.56–3.80 (m, 4H), 7.09–7.91 (m, 7H); $^{13}$C NMR (CDCl$_3$) δ20.95, 25.89, 26.05, 31.66, 32.00, 32.23, 32.89, 33.16, 34.85, 36.38, 39.78, 61.43, 95.82, 107.05, 111.46, 117.19, 122.84, 125.19, 129.39, 136.52, 138.86, 147.31, 150.84, 155.96, 160.36, 160.51, 169.24.

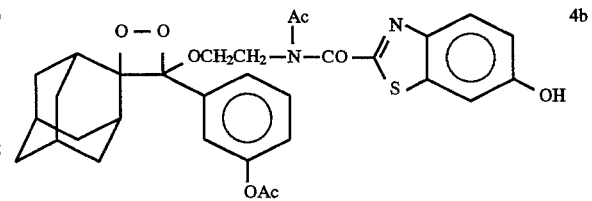

4b 4-(3-Acetoxyphenyl)-4-(2-(O-fluorescein)ethoxy)spiro[1,2-dioxetane-3,2-'adamantane](6).

[(3-Acetoxyphenyl)(2-(O-fluorescein)ethoxy)methylene]adamantane(5) (35 mg 0.05 mmol) was dissolved in 1 mL of 1,4-dioxane-d$_8$ in an NMR tube. Sensitox (20 mg) was added and an oxygen bubbler connected. Oxygen was passed slowly through the solution for 5 min and the apparatus immersed in a half-silvered Dewar flask containing ice/water. The sample was irradiated with a 1000 W sodium lamp and a UV cut-off filter while oxygen was bubbled continuously. After 45 min of photooxygenation, $^1H$, and $^{13}C$ NMR revealed complete conversion of the alkene to its corresponding dioxetane (36.7 mg 0.05 mmol, 100%).

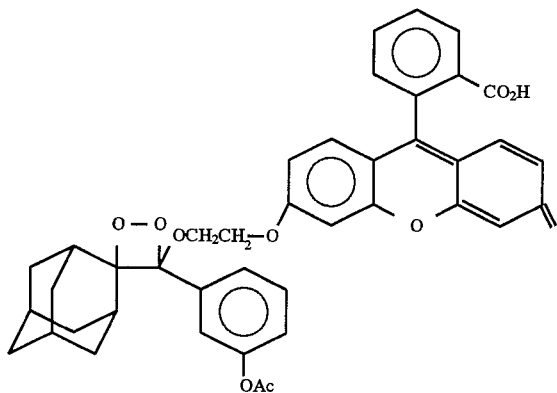

4-(2-(N-(6-hydroxybenzothiazoate-2-carbonyl)amino)ethoxy)-4-(3-β-D-galactopyranosykphenyl)spiro[1,2-dioxetane-3,2'-adamantane](8).

Alkene 7 (50 mg 0.075 mmol) was photooxygenated in 4 mL of a 1:1 mixture of methylene chloride and acetone at −78° C. with a 1000 W high pressure sodium lamp using 100 mg of Sensitox. The reaction was stopped after 1 hr and filtration and removal of the solvent gave a white solid as the product: $^1H$ NMR δ1.57–1.9 (m, 12H), 2.2 (s, 1H), 3.08 (s, 1H), 3.37 (t, 1H), 3.55–3.99 (m, 9H), 4.97 (m, 1H), 6.35 (bs, 4H), 3.89–7.9 (m, 8H), 8.41 (bs, 1H), 9.51 (s, 1H); $^{13}C$ NMR δ26.47, 26.66, 32.04, 32.39, 32.50, 33.29, 33.73, 35.07, 36.69, 39.97, 61.56, 61.91, 69.44, 71.77, 74.33, 76.09, 95.49, 101.83, 102.15, 107.33, 111.88, 117.70, 123.34, 125.47, 129.86, 137.08, 139.17, 147.46, 157.76, 158.42, 160.66, 161.32.

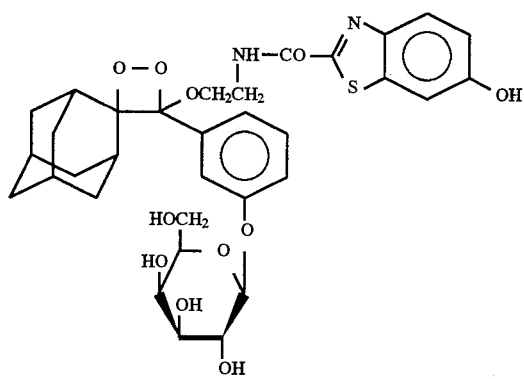

4-(3-Phosphatephenyl)-4-(2-(O-fluorescein)ethoxy)spiro[1,2-dioxetane-3,2'-adamantane](10) and 4-(2-(N-(6-hydroxybenzothiazoate-2-carbonyl)amino)ethoxy)-4-(3-phosphatephenyl)spiro[1,2-dioxetane-3,2'-adamantane](12) are prepared using the photooxygenation procedures described above from alkenes 9 and 11, respectively.

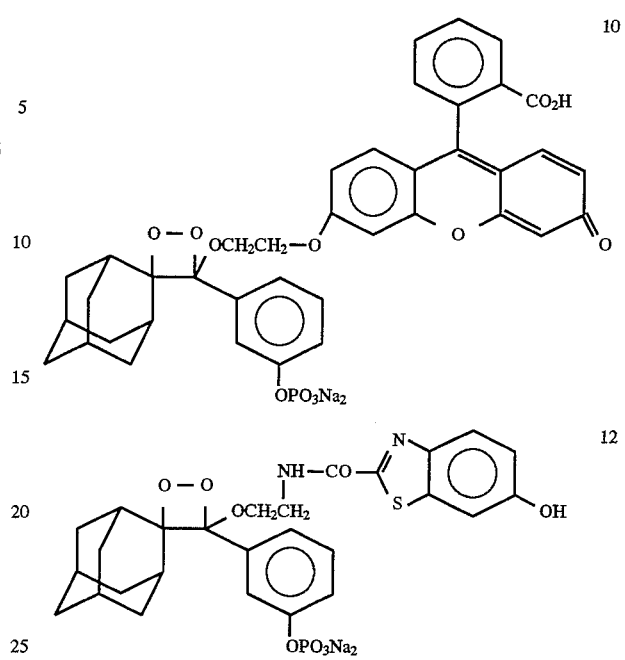

Determination of Chemiluminescence Quantum Yields

The chemiluminescence quantum yield ($\phi_{CL}$)for the decomposition of dioxetanes is defined as the ratio of einsteins of chemiluminescence emitted to moles of dioxetane decomposed. This quantity is often expressed as an efficiency where chemiluminescence efficiency (%)=$\phi_{CL}$. Sufficient energy is released during the reaction from the reaction enthalpy ($\Delta H_R$) plus the Arrhenius activation energy ($E_a$) to populate the singlet exalted state of one of the carbonyl cleavage products. Therefore, the maximum quantum yield is 1.0. Another parameter of interest is the chemiexcitation quantum yield ($\phi_{CE}$) which is defined as the ratio of excited states formed to dioxetane decomposed. The chemiexcitation quantum yield is related to the chemiluminescence quantum yield via the fluorescence quantum yield of the dioxetane cleavage ($\phi_F$) through the equation:

$$\phi_{CL}=\phi_{CE}\times\phi_F.$$

The same procedure as those employed in the measurement of the decay kinetics was used for the determination of chemiluminescence quantum yields with the following modifications. An accurately measured aliquot of a dioxetane stock solution of known concentration was added to 3 mL of the pre-thermostatted organic solvent or aqueous buffer. The reaction was then triggered by adding the appropriate chemical reagent or enzyme. The total light intensity was integrated by a photon-counting luminometer using an RCA A-31034A gallium-arsenide PMT cooled to −78° C. Light intensity was converted to photons by reference to a calibration factor based on the accurately known quantum yield of the chemiluminescent reaction of luminol with base in aerated DMSO. The luminol reaction has been determined to have a chemiluminescence quantum yield of 0.011 (1.1%) (J. Lee and H. H. Seliger, Photochem. Photobiol., 15, 227 (1972); P. R. Michael and L. R. Faulkner, Anal. Chem., 48, 1188 (1976)).

Acquisition of Chemiluminescence Spectra

Spectra of the chemiluminescence from chemically or enzymatically triggered dioxetanes were obtained by conducting the reaction in a 1-cm square quartz cuvette in the sample compartment of a Spex Fluorolog spectrofluorometer at ambient temperature. Correction for the decay of the chemiluminescence intensity during the wavelength scan was made by accumulating the spectrum in a ratio mode so that the observed spectrum was divided by the signal from an auxiliary detector (EMI 9781B) which measures the total signal as a function of time. The monochromator bandpass was typically 18 nm. For weakly emitting samples, several identical scans were performed and added together to improve the signal-to-noise ratio.

Triggering of Dioxetanes

1. Chemical Triggering of the Chemiluminescence of Hydroxy-Substituted Dioxetane 2a and Acetoxy-Substituted Dioxetane 2b in DMSO and Aqueous Solution. Treatment of $10^{-4}$M solutions of dioxetanes 2a and 2b in DMSO at room temperature (25° C.) with an excess of tetra-n-butylammonium hydroxide or tetra-n-butylammonium fluoride resulted in intense blue chemiluminescence which decayed over several minutes. The emission maximum for the chemiluminescence is 470 nm. The fluorescence of the anion of the cleavage product (methyl 3-hydroxybenzoate, MHB) is identical to the chemiluminescence spectrum. These results demonstrate that the chemiluminescence process involves: (a) base triggering to yield the unstable aryloxide form of the dioxetane, (b) subsequent cleavage of this species to generate MHB in the singlet excited state, and (c) fluorescence of MHB to yield the luminescence with an overall efficiency which can be as high as 25%. These results are comparable to those previous reported for fluoride-triggered chemiluminescence of the corresponding silyloxy-substituted dioxetane (A. P. Schaap, patent application filed Jul. 15, 19986; A. P. Schaap, T. S. Chen, R. S. Handley, R. DeSilva, and B. P. Giri, *Tetrahedron Lett.*, 1155 (1987)).

In contrast, chemical triggering of 2a and 2b in aqueous solution with various bases including NaOH results in extremely low levels of luminescence (0.0008% chemiluminescence efficiency). This low value results from the fact that the ester MHB is essentially non-fluorescent in the aqueous environment.

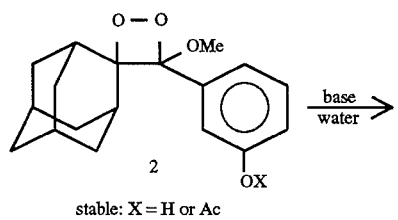

stable: X = H or Ac

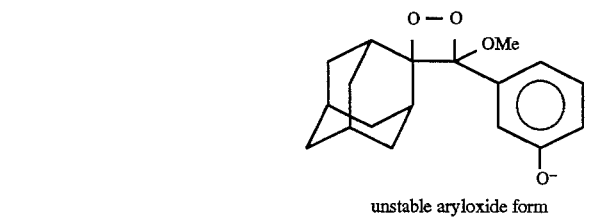

unstable aryloxide form

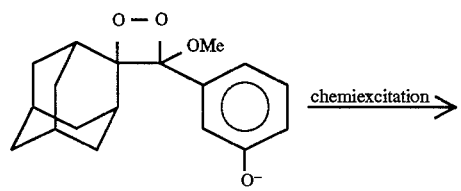

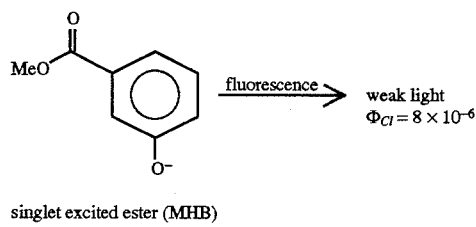

singlet excited ester (MHB)

2. Chemical Triggering of the Chemiluminescence of Dioxetanes 4 and 6: Enhanced Chemiluminescence Efficiency via Intramolecular Energy Transfer to a Tethered Fluorescer.

It has now been discovered that chemiluminescence efficiencies from triggerable dioxetanes can be dramatically enhanced through intramolecular energy transfer to a fluorescent group that is chemically attached or tethered to the excited cleavage product of the dioxetane. In these new compounds, the aryloxide-substituted dioxetane is utilized for the "energy-generating" function and the "light-emitting" process is carried out by an efficiently fluorescent group that is tethered to the excited cleavage product.

Normally, with dioxetanes such as 2a and 2b (shown above), removal of the protecting group X by a chemical reagent or an enzyme produces the unstable form of the dioxetane which cleaves to generate the singlet excited ester. Emission from this species provides direct chemiluminescence. However, in the presence of a lower energy fluorescer that is tethered to the excited product through a series of connecting atoms such as in dioxetanes 4 and 6, intramolecular energy transfer can yield the excited state of the fluorescer (for example, see Scheme 1). Emission from this moiety affords energy-transfer chemiluminescence. With favorable energetics for energy transfer and an optimum number of atoms for the length of the tether, the efficiency of energy-transfer ($\phi_{ET}$) can approach unity. Further, if the fluorescer is selected to have a higher $\phi_F$ than th energy donor, the overall chemiluminescence can be enhanced. Additionally, the color of the luminescence can be selected from blue to red with the appropriate tethered fluorescer.

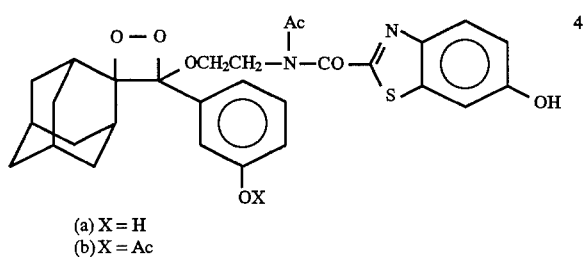

(a) X = H
(b) X = Ac

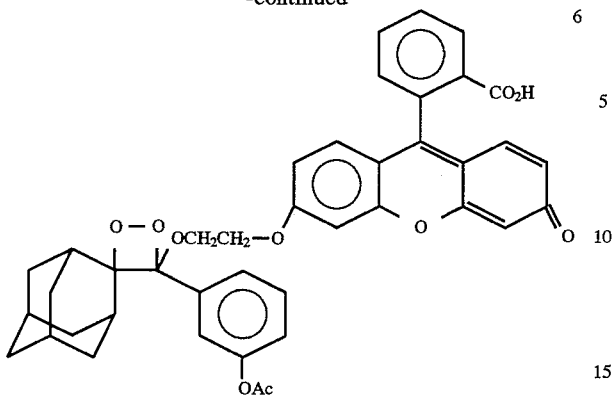

Chemical triggering experiments with dioxetanes 4 and 6 illustrate the large increases in chemiluminescence efficiencies that can be achieved by with these novel dioxetanes (see Table 1). For example, the fluoride-triggered reaction in DMSO of dioxetane 4b gives an intense blue-green emission with an efficiency of 49%, double the efficiency of dioxetane 2b under the same conditions. Similar results are obtained with base and fluoride triggering of the hydroxy-substituted dioxetane 4a. Even larger enhancements are observed for reactions conducted in aqueous solutions with increases for tethered dioxetanes 4 and 6 of up to 450-fold, compared to 2a and 2b (Table 1). As shown by the spectra in FIGS. 1, 3, and 4, the normal emission at 470 nm is quenched and replaced by the emission of the tethered fluorescer, demonstrating the very high efficiency for intramolecular energy transfer in these novel compounds. These figures also illustrate the enhancement in chemiluminescence efficiency that is achieved in both the chemical and enzymatic triggering of the dioxetanes bearing tethered fluorescers.

TABLE 1

Chemiluminescence Efficiencies (%) for Acetoxy-Substituted Dioxetanes

| Triggering Conditions | Dioxetane 2b | Dioxetane 4b | Dioxetane 6 |
|---|---|---|---|
| Enzymatic: aryl esterase, pH 9.2 | 0.0012 | 0.29 | 0.39 |
| Chemical: aqueous NaOH | 0.00084 | 0.20 | 0.38 |
| Chemical: aqueous CTAB, NaOH | 0.017 | 2.2 | 1.4 |
| Chemical: DMSO, fluoride | 25 | 49 | — |

3. Enzymatic Triggering of the Chemiluminescence of Dioxetanes 4b and 6: Enhanced Chemiluminescence Efficiency via Intramolecular Energy Transfer to a Tethered Fluorescer.

Aryl esterase (carboxyl esterase)from porcine liver was obtained from Sigma Chemical Co. as a suspension in 3.2M $(NH_4)_2SO_4$. In a typical experiment, 50 μL of a $2.56 \times 10^{-3}$M stock solution of the dioxetane in 221 buffer was added to 3 mL of 221 buffer (0.75M, pH 9.2) giving a final dioxetane concentration of $4.3 \times 10^{-5}$M. Injection of a 10 μL aliquot of diluted enzyme into the solution at 37° C. resulted in chemiluminescence. The chemiluminescence efficiencies for enzymatic triggering of tethered dioxetanes 4b and 6 were found to be 0.29 and 0.39% respectively. These values represent enhancements of 240- and 325-fold, respectively, compared to the direct luminescence obtained from the reaction of dioxetane 2b under the same conditions.

Figure 5:
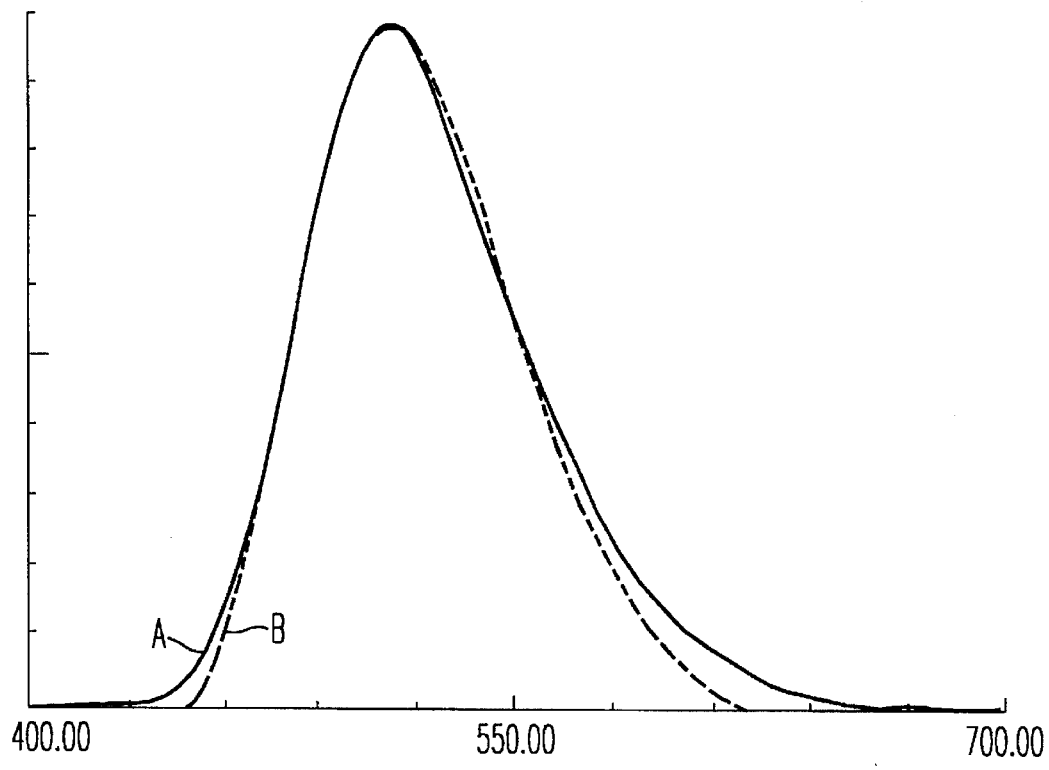
FIG. 5 is a graph wherein curve A (____) shows the chemiluminescence spectrum from enzymatic triggering of tethered dioxetane 4b in 221 buffer (pH 9.2) with aryl esterase ($\lambda_{max}$=519 nm); and curve B (---) shows the fluorescence spectrum of the cleavage product under the same conditions.

The chemiluminescence spectra in FIG. 4 show the normal weak emission (Curve A, λ. =470 nm) for 2b and the energy-transfer chemiluminescence (Curve B, λ=519 nm) derived from 4b with aryl esterase. A comparison of the chemiluminescence spectrum of the enzymatic triggering of dioxetane 4b with the fluorescence spectrum of the cleavage product under the same conditions demonstrates that the emission does, in fact, arise from the tethered fluorescer (FIG. 5). The kinetics of the reactions with 4b and 6 indicates that the tethered fluorescers do not significantly inhibit the enzymatic turn-over of the substrate. Further, the enzyme does not seem to interfere with intramolecular energy transfer.

4. Enzymatic Triggering of the Chemiluminescence of Dioxetane 8: Enhanced Chemiluminescence Efficiency via Intramolecular Energy Transfer to a Tethered Fluorescer.

β-Galactosidase (Sigma) was reacted with solutions of the galactopyranosyl-substituted dioxetanes 2c and 8. In a typical experiment, 100 μL of enzyme solution was added to 3 mL of dioxetane solution (0.0028 mmol) in phosphate buffer (pH 7.2) at 37° C. The solutions were incubated for 5 min after which time NaOH was added to increase the pH of the solutions to trigger the luminescence of the deprotected dioxetane (the hydroxy form). The chemiluminescence intensity with dioxetane 8 was enhanced by over 200-fold compared to dioxetane 2c. These results further illustrate the significant increases in light yields that can be obtained through the use of intramolecular energy transfer to tethered fluorescers.

Figure 6:
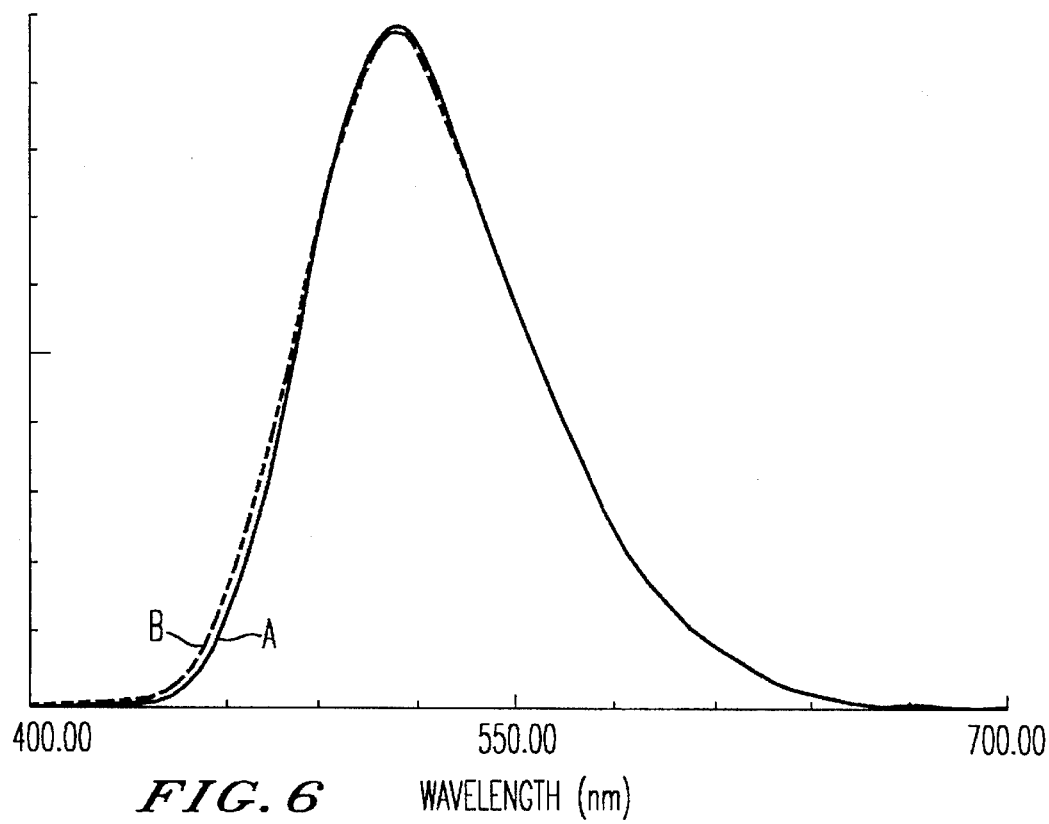
FIG. 6 is a graph wherein curve A (____) shows the chemiluminescence spectrum produced by enzymatic triggering with β-galactosidase of tethered dioxetane 8 in phosphate buffer (pH 7.2) followed by addition of 10N NaOH to induce the luminescence ($\lambda_{max}$=519 nm); and curve B (---) shows the fluorescence spectrum of the cleavage product under the same conditions.

A comparison of the chemiluminescence spectrum of the enzymatic triggering of dioxetane 8 with the fluorescence spectrum of the cleavage product under the same conditions demonstrates again that the emission does, in fact, arise from the tethered fluorescer (FIG. 6).

Similar spectroscopic results are obtained with the phosphate-substituted dioxetanes 10 and 12 with enhanced chemiluminescence intensities compared to dioxetane 2d.

SCHEME 1: MECHANISM OF CHEMICAL- AND ENZYME-TRIGGERED ENERGY-TRANSFER CHEMILUMINESCENCE IN AQUEOUS SOLUTION

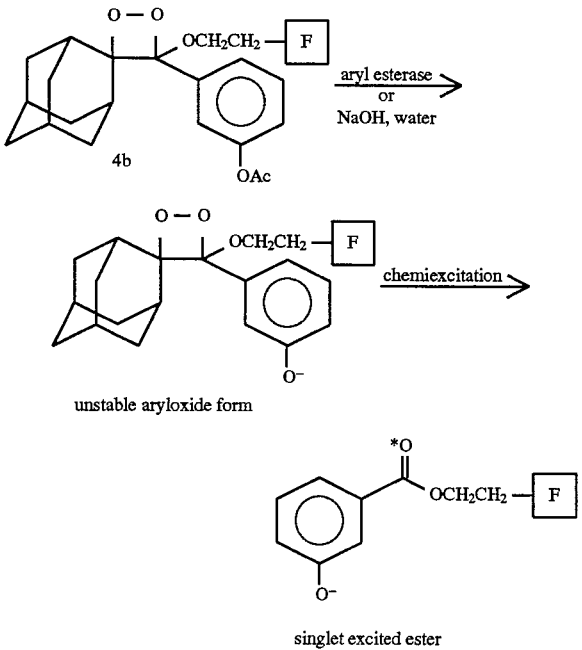

SCHEME 1: MECHANISM OF CHEMICAL- AND ENZYME-TRIGGERED ENERGY-TRANSFER CHEMILUMINESCENCE IN AQUEOUS SOLUTION

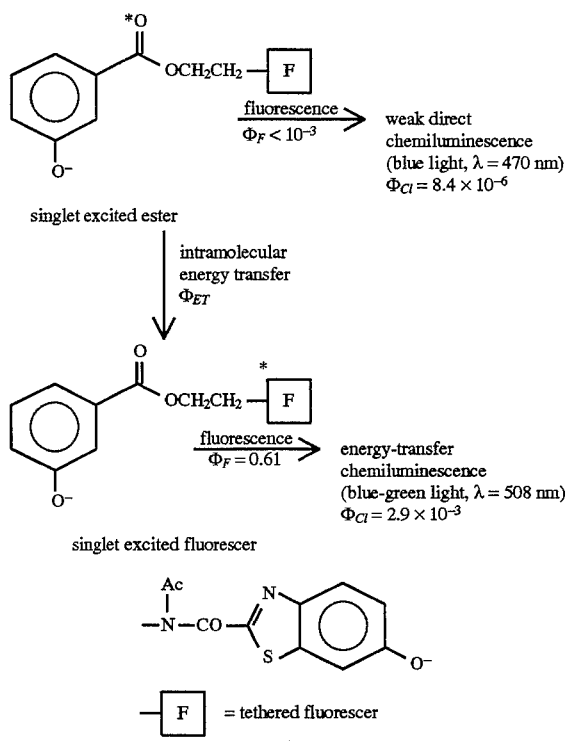

Under the conditions of the reactions, the fluorescer exists in the ionized form.

In addition to the specific alkenes and dioxetanes bearing OX groups on the aryl ring in the meta position described herein, the corresponding para and ortho isomers can be prepared by similar procedures. Such compounds are for example for the dioxetanes:

Dioxetanes 4-(4-Hydroxyphenyl)-4-methoxyspiro[1,2-dioxetane-3,2'-adamantane]

4-(4-Acetoxyphenyl)-4-methoxyspiro[1,2-dioxetane-3,2'-adamantane]

4-(4-Phosphatephenyl)-4-methoxyspiro[1,2-dioxetane-3,2'-adamantane], salt 4-(4-β-D-Galactopyranosylphenyl)-4-methoxyspiro[1,2-dioxetane-3,2'-adamantane]

4-(2-(N-Acetyl-N-(6-hydroxybenzothiazole-2-carbonyl)amino)ethoxy)-4-(4-hydroxyphenyl)spiro[[1,2-dioxetane-3,2-adamantane]

4-(4-Acetoxyphenyl)-4-(2-(N-acetyl-N-(6-hydroxybenzothiazole-2-carbonyl)amino)ethoxy)spiro[1,2-dioxetane-3,2'-adamantane]

4-(4-Acetoxyphenyl)-4-(2-(O-fluorescein)ethoxy)spiro[1,2-dioxetane-3,2-'adamantane]

4-(2-(N-(6-Hydroxybenzothiazole-2-carbonyl)amino)ethoxy)-4-(4-β-D-galactopyranosylphenyl)spiro[1,2-dioxetane-3,2'-adamantane]

4-(4-Phosphatephenyl)-4-(2-(O-fluorescein)ethoxy)spiro[1,2-dioxetane-3,2'-adamantane], salt 4-(2-(N-(6-Hydroxybenzothiazole-2-carbonyl)amino)ethoxy)-4-(4-phosphatephenyl)spiro[1,2-dioxetane-3,2'-adamantane], salt for the alkenes:

[(4-Hydroxyphenyl)methoxymethylene]adamantane

[(4-Acetoxyphenyl)methoxymethylene]adamantane

[(4-Phosphatephenyl)methoxymethylene]adamantane, salt

[(4-(β-D-Galactopyranosyl)phenyl)methoxymethylene]adamantane

{[2-(N-(6-tert-Butyldimethylsilyloxybenzothiazole-2-carbonyl)amino)ethoxy][4-hydroxyphenyl]methylene}adamantane {[2-(N-Acetyl-N-(6-hydroxybenzothiazole-2-carbonyl)amino)ethoxy][4-hydroxyphenyl]methylene}adamantane {[4-Acetoxyphenyl][2-(N-acetyl-N-(6-hydroxybenzothiazole-2-carbonyl)amino)ethoxy]methylene}adamantane

[(4-Acetoxyphenyl)(2-(O-fluorescein)ethoxy)methylene]adamantane

{[2-(N-(6-Hydroxybenzothiazole-2-carbonyl)amino)ethoxy][4-β-D-galactopyranosylphenyl]methylene}adamantane

[(4-Phosphatephenyl)(2-(O-fluorescein)ethoxy)methylene]adamantane, salt

{[2-(N-(6-Hydroxybenzothiazole-2-carbonyl)amino)ethoxy][4-phosphatephenyl]methylene}adamantane, salt In addition to the specific examples described herein, a wide variety of standard literature methods can be employed for the coupling of fluorescers to the alkene or the dioxetane. These reactions include but are not limited to: nucleophilic displacements, electrophilic substitutions, additions to alkenes and carbonyl compounds, nucleophilic addition to carboxylic acid derivatives, and additions to isothiocyanates and isocyanates.

It is intended that the foregoing description be only illustrative of the present invention and that the invention be limited only by the hereinafter appended claims.

We claim:

1. 4-(3-β-D-Galactopyranosylphenyl)-4-methoxyspiro[1,2-dioxetane-3,2'-adamantane].

* * * * *

UNITED STATES PATENT AND TRADEMARK OFFICE
CERTIFICATE OF CORRECTION

PATENT NO. : 5,652,345
DATED : JULY 29, 1997
INVENTOR(S) : ARTHUR PAUL SCHAAP, ET AL.

It is certified that error appears in the above-identified patent and that said Letters Patent is hereby corrected as shown below:

Cover page under OTHER PUBLICATIONS, column 2, line 20, J.E. McMury" should read - -J.E. McMurry- -.

Column 5, line 66, "McMury" should read - -McMurry- -.

Column 10, line 12, "singlet-single" should read - -singlet-singlet- -.

Column 12, lines 7-10,

"
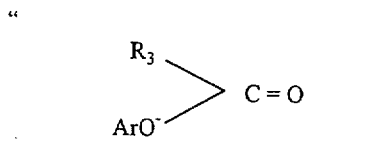
"

should read

- -
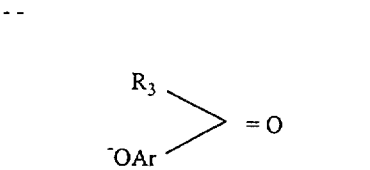
- -.

UNITED STATES PATENT AND TRADEMARK OFFICE
CERTIFICATE OF CORRECTION

PATENT NO. : 5,652,345
DATED : JULY 29, 1997
INVENTOR(S) : ARTHUR PAUL SCHAAP, ET AL.

It is certified that error appears in the above-identified patent and that said Letters Patent is hereby corrected as shown below:

Column 26, line 24, "acetane/benzene" should read - -acetate/benzene- -.

Column 34, line 47, "th" should read - -the - -.

Signed and Sealed this

Twenty-ninth Day of August, 2000

Attest:

Q. TODD DICKINSON

*Attesting Officer*  *Director of Patents and Trademarks*